(12) United States Patent
Lee et al.

(10) Patent No.: US 11,591,645 B2
(45) Date of Patent: Feb. 28, 2023

(54) EVALUATION OF PERFORMANCE OF COMPONENTS USING A PAIR OF DIMER-FORMING PRIMERS

(71) Applicant: SEEGENE, INC., Seoul (KR)

(72) Inventors: Young Jo Lee, Seoul (KR); Dae Young Kim, Seoul (KR)

(73) Assignee: SEEGENE, INC., Seoul (KR)

( * ) Notice: Subject to any disclaimer, the term of this patent is extended or adjusted under 35 U.S.C. 154(b) by 0 days.

(21) Appl. No.: 16/642,179

(22) PCT Filed: Aug. 31, 2018

(86) PCT No.: PCT/KR2018/010182
§ 371 (c)(1),
(2) Date: Feb. 26, 2020

(87) PCT Pub. No.: WO2019/045532
PCT Pub. Date: Mar. 7, 2019

(65) Prior Publication Data
US 2021/0071230 A1    Mar. 11, 2021

(30) Foreign Application Priority Data
Aug. 31, 2017    (KR) .......................... 10-2017-0111441

(51) Int. Cl.
*C12Q 1/68*    (2018.01)
*C12Q 1/686*    (2018.01)

(52) U.S. Cl.
CPC .................................... *C12Q 1/686* (2013.01)

(58) Field of Classification Search
CPC ...................................................... C12Q 1/68
See application file for complete search history.

(56) References Cited

U.S. PATENT DOCUMENTS

| | | | |
|---|---|---|---|
| 5,210,015 A | 5/1993 | Gelfand et al. |
| 5,432,272 A | 7/1995 | Benner |
| 5,538,848 A | 7/1996 | Livak et al. |
| 5,691,142 A | 11/1997 | Dahlberg et al. |
| 5,789,167 A | 8/1998 | Konrad |
| 5,965,364 A | 10/1999 | Benner |

(Continued)

FOREIGN PATENT DOCUMENTS

| | | |
|---|---|---|
| KR | 10-2017-0121700 A | 11/2017 |
| WO | WO-92/20702 A1 | 11/1992 |

(Continued)

OTHER PUBLICATIONS

Primer Dimer, Wikipedia, available at https://en.wikipedia.org/wiki/Primer_dimer, accessed Apr. 13, 2021.*

(Continued)

*Primary Examiner* — Aaron A Priest
(74) *Attorney, Agent, or Firm* — Harness, Dickey & Pierce, P.L.C.

(57) ABSTRACT

The present invention relates to the evaluation of the performance of a component using a pair of dimer-forming primers. The method using the pair of dimer-forming primers according to the present invention can be used not only for evaluating the performance of components including a nucleic acid polymerase but also as an internal control in the detection of a target nucleic acid sequence.

10 Claims, 5 Drawing Sheets

Specification includes a Sequence Listing.

(i) Hybridization between two primers (ii) Extension & Signal generation

(56) References Cited

U.S. PATENT DOCUMENTS

| | | | |
|---|---|---|---|
| 6,001,611 A * | 12/1999 | Will | C12Q 1/686 435/91.2 |
| 6,001,983 A | 12/1999 | Benner | |
| 6,037,120 A | 3/2000 | Benner | |
| 6,117,635 A | 9/2000 | Nazarenko et al. | |
| 6,174,670 B1 | 1/2001 | Wittwer et al. | |
| 6,194,149 B1 | 2/2001 | Neri et al. | |
| 6,323,337 B1 * | 11/2001 | Singer | C07H 21/00 435/6.1 |
| 6,326,145 B1 | 12/2001 | Whitcombe et al. | |
| 6,358,691 B1 | 3/2002 | Neri et al. | |
| 6,977,295 B2 | 12/2005 | Belotserkovskii et al. | |
| 7,309,573 B2 | 12/2007 | Sorge | |
| 7,348,141 B2 | 3/2008 | French et al. | |
| 7,537,886 B1 | 5/2009 | Nazarenko et al. | |
| 2006/0177841 A1 | 8/2006 | Wangh et al. | |
| 2008/0038734 A1 | 2/2008 | Sorge et al. | |
| 2009/0142764 A1 | 6/2009 | Hennessy et al. | |
| 2010/0184067 A1 | 7/2010 | Abe et al. | |
| 2014/0377767 A1 | 12/2014 | Gong et al. | |

FOREIGN PATENT DOCUMENTS

| | | | |
|---|---|---|---|
| WO | WO-98/22489 A1 | 5/1998 | |
| WO | WO-98/39352 A1 | 9/1998 | |
| WO | WO-99/14226 A2 | 3/1999 | |
| WO | WO-2011/078441 A1 | 6/2011 | |
| WO | WO-2012/096523 A2 | 7/2012 | |
| WO | WO-2013/115442 A1 | 8/2013 | |
| WO | WO-2013/140107 A1 | 9/2013 | |
| WO | WO-2014/104818 A1 | 7/2014 | |
| WO | WO-2015147377 A1 * | 10/2015 | C12Q 1/6858 |
| WO | WO-2017/088169 A1 | 6/2017 | |

OTHER PUBLICATIONS

Tyagi et al, Nature Biotechnology v.14 Mar. 1996.
French DJ et al., Mol. Cell Probes, 15(6):363-374(2001).
Bernard et al, 147-148 Clin Chern 2000; 46.
Nazarenko et al, 2516-2521 Nucleic Acids Research, 1997, v.25 No. 12.
Whitcombe et al, 804-807, Nature Biotechnology v.17 Aug. 1999.
Salvatore et al., Nucleic Acids Research, 2002 (30) No. 21 e122.
Johansson et al., J. Am. Chem. Soc 2002 (124) pp. 6950-6956.
Drobyshevetal, *Gene* 188: 45(1997).
Kochinsky and Mirzabekov *Human Mutation* 19:343(2002).
Livshits et al *J. Biomol. Structure Dynam*. 11:783(1994).
Howell et al *Nature Biotechnology* 17:87(1999).
Richardson, C. D. et al. (1964) J. Biol. Chem. 239, 222-232.
Griep, M. A. (1995) Anal. Biochem. 232, 180-189.
Seville, M., et al. (1996) Biotechniques 21, 664, 668, 670, 672.
Tveit, J. et al. (2001) Anal. Biochem. 289, 96-98.
Yu, Liming, et al. (2002) Biotechniques 33, 938-941.
Ma, C. et al. (2006) Anal. Biochem. 353, 141-143).
Luo, X. et al. (2011) Electroanalysis 23 923-926.
International Search Report from corresponding PCT Application No. PCT/KR2018/010182, dated Apr. 10, 2019.

* cited by examiner (i) Hybridization between two primers (ii) Extension & Signal generation

EVALUATION OF PERFORMANCE OF COMPONENTS USING A PAIR OF DIMER-FORMING PRIMERS

CROSS-REFERENCE TO RELATED APPLICATIONS

This application is a national phase application of PCT Application No. PCT/KR2018/010182 filed on Aug. 31, 2018, which claims priority to Korean Patent Application No. 10-2017-0111441 filed on Aug. 31, 2017. The entire disclosures of the applications identified in this paragraph are incorporated herein by reference.

FIELD OF THE INVENTION

The present invention relates to the evaluation of the performance of a component, particularly a component associated with amplification reaction, using a pair of dimer-forming primers.

BACKGROUND OF THE INVENTION

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. The exemplified methods by use of hybridization between labeled probes and target nucleic acid sequences include Molecular beacon method using dual-labeled probes with hairpin structure (Tyagi et al, Nature Biotechnology v.14 MARCH 1996), HyBeacon method (French D J et al., Mol. Cell Probes, 15(6):363-374 (2001)), Hybridization probe method using two probes labeled each of donor and acceptor (Bernard et al, 147-148 Clin Chem 2000; 46) and Lux method using single-labeled oligonucleotides (U.S. Pat. No. 7,537,886). TaqMan method (U.S. Pat. Nos. 5,210,015 and 5,538,848) using dual-labeled probes and its cleavage by 5'-nuclease activity of DNA polymerase is also widely employed in the art.

The exemplified methods using labeled primers include Sunrise primer method (Nazarenko et al, 2516-2521 Nucleic Acids Research, 1997, v.25 no.12, and U.S. Pat. No. 6,117,635), Scorpion primer method (Whitcombe et al, 804-807, Nature Biotechnology v.17 AUGUST 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. Nos. 5,691,142, 6,358,691 and 6,194,149), PTOCE (PTO cleavage AND extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (WO 2014/104818).

There are a number of components involved in amplification and detection of target nucleic acid sequences. Examples of the components include, without limitation, chemical components such as a primer, a probe, a label, a nucleic acid polymerase, a buffer, dNTPs, a salt, and an additive (e.g., BSA, DMSO, betaine, and a non-ionic surfactant); physical components such as an amplification vessel (e.g., a tube), a thermocycler and a detector; and other components such as a sample (particularly components included in the sample), prepared for detection of a nucleic acid sequence of interest.

The performance of such components has a significant effect on both amplification and detection of a target nucleic acid sequence.

As an example, the performance of a nucleic acid polymerase involved in extending a primer directly affects the amplification of a target nucleic acid sequence to be detected. Nucleic acid polymerases with good performance can produce amplified products at a detectable level with short cycles of PCR; whereas nucleic acid polymerases with poor performance may not yield amplified products at a detectable level even with long cycles of PCR.

As another example, the performance of an amplification device (particularly, a detector) involved in detecting a signal from a target nucleic acid sequence affects the analysis of the target signal. Amplification devices with good performance can detect all of the generated signal intensities; whereas amplification devices with poor performance may detect only some of the generated signal intensities.

The performance of components may vary depending upon various factors such as variations in performance during manufacture and deterioration of performance during storage.

For example, a decrease in polymerization activity of a nucleic acid polymerase due to improper storage conditions and a long storage period causes insufficient amplification of a target nucleic acid sequence, which may result in false-negative results even in the presence of the target nucleic acid sequence in a sample. Furthermore, variation in activity of a nucleic acid polymerase may lead to different results in the analysis for the same sample. This may be equally problematic in other components such as amplification devices.

Therefore, in order to obtain more accurate and consistent results, it would be desirable to accurately evaluate the performance of components and to use those with the same or similar performance based on the evaluation.

Typically, the evaluation of the performance of components has been performed by real-time PCR methods using a template DNA from a standard strain and primers and a labeled probe for amplifying the template DNA. However, these methods have serious drawbacks in accurately determining the performance of actual components, as follows: (i) difficulty in optimizing reaction conditions and sequences of primers and a probe used; (ii) possibility of non-specific interference between components used; (iii) low sensitivity of the reaction.

Accordingly, there remains a need to develop a novel method for evaluating the performance of a component to solve these drawbacks.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY OF THE INVENTION

The present inventors have endeavored to develop a method for evaluating the performance of various components used in an amplification reaction (e.g., components in an amplification composition or components in an amplification device). In particular, the present inventors have sought to improve the non-specific interference between components and low sensitivity that are problematic in the conventional performance evaluation. As a result, the present inventors have confirmed that the performance of components can be evaluated in a more accurate and sensitive manner by an amplification reaction using a dimer-forming primer pair without a template.

Accordingly, it is an object of this invention to provide a method for evaluating the performance of a component in an amplification composition or an amplification device by an amplification reaction using a pair of dimer-forming primers.

It is another object of this invention to provide a kit for evaluating the performance of a component in an amplification composition or an amplification device.

Other objects and advantages of the present invention will become apparent from the detailed description to follow taken in conjugation with the appended claims and drawings.

DETAILED DESCRIPTION OF THIS INVENTION

Figure 1:
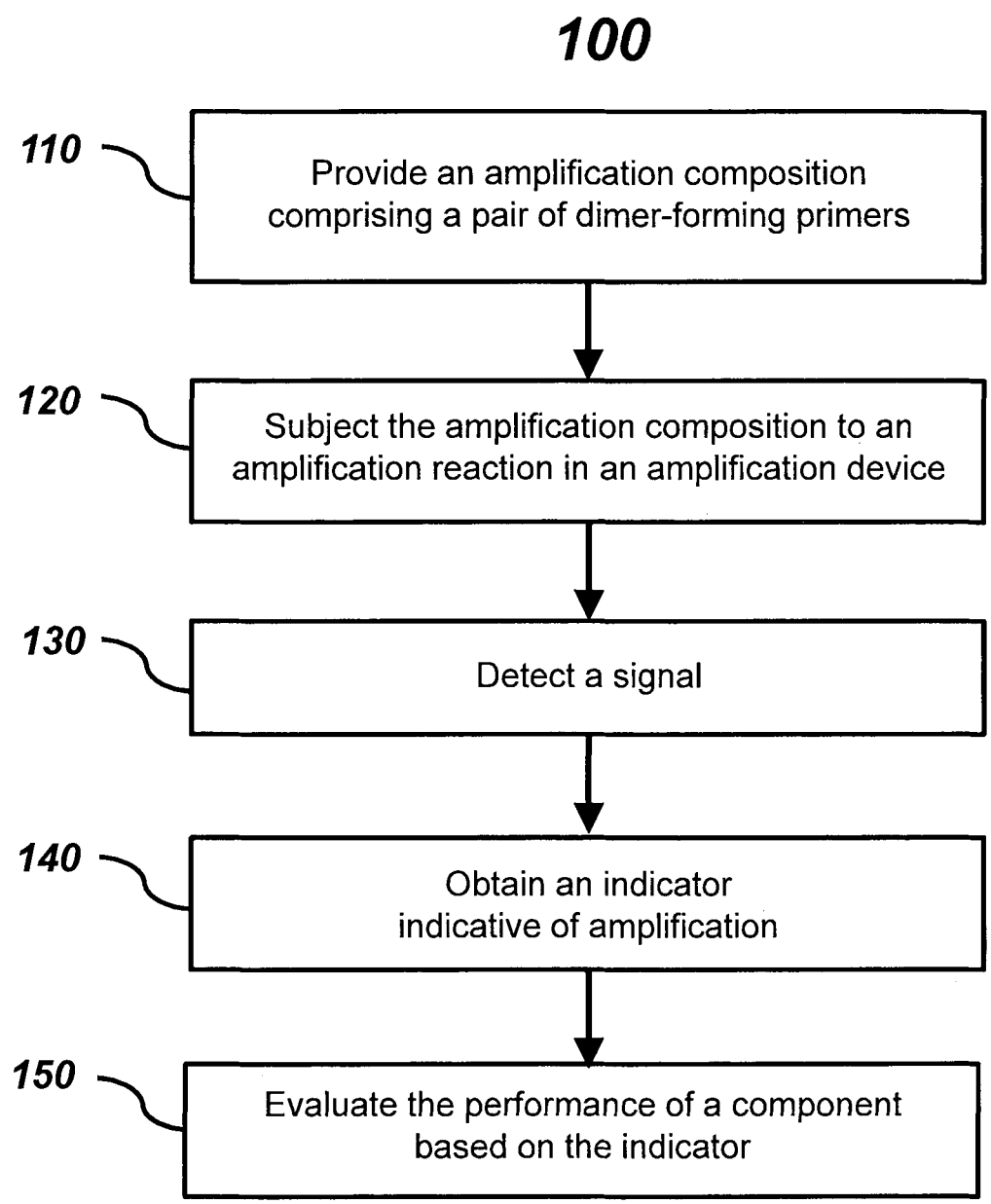
FIG. 1 is a flow chart 100 representing a process for evaluating the performance of a component by an amplification reaction using a pair of dimer-forming primers in accordance with an embodiment of the present invention.

I. Evaluation of the Performance of a Component Using a Pair of Dimer-Forming Primers In one aspect of this invention, there is provided a method for evaluating the performance of a component in an amplification composition or an amplification device by an amplification reaction using a pair of dimer-forming primers, comprising the steps of:

(a) providing an amplification composition comprising a pair of dimer-forming primers; wherein the pair of dimer-forming primers comprises a first primer and a second primer; wherein the first primer and the second primer each comprise a 3'-dimer-forming portion, and a nucleotide sequence of the 3'-dimer-forming portion in the first primer is complementary to a nucleotide sequence of the 3'-dimer-forming portion in the second primer;

(b) subjecting the amplification composition to an amplification reaction in an amplification device; wherein the first primer and the second primer form a dimer through hybridization between the 3'-dimer-forming portions under amplification conditions, and are each extended by a nucleic acid polymerase to form an extended duplex; wherein a detectable signal is provided in a dependent manner on the presence of the extended duplex;

(c) detecting the detectable signal during or after the amplification reaction;

(d) obtaining an indicator indicative of amplification from the detected signal; and (e) evaluating the performance of the component based on the indicator obtained.

The present inventors have endeavored to develop a method for evaluating the performance of various components used in an amplification reaction (e.g., components in an amplification composition or components in an amplification device). In particular, the present inventors have sought to improve the non-specific interference between components and low sensitivity that are problematic in the conventional performance evaluation. As a result, the present inventors have confirmed that the performance of components can be evaluated in a more accurate and sensitive manner by an amplification reaction using a dimer-forming primer pair without a template.

The present invention relates to a method for evaluating the performance of a component. The component is one used in an amplification reaction. The component is one used in an amplification reaction of a nucleic acid sequence. The component is one used in a real-time amplification reaction of a nucleic acid sequence.

The component to be evaluated may be selected from components in an amplification composition and component in an amplification device. The component to be evaluated may be selected by a user of this invention. The component to be evaluated may be selected prior to performing the method of the present invention.

In one embodiment, the component to be evaluated is a nucleic acid polymerase.

In another embodiment, the component to be evaluated is a label.

In still another embodiment, the component to be evaluated is a sample.

In still another embodiment, the component to be evaluated is an amplification vessel.

In still another embodiment, the component to be evaluated is a thermocycler and/or a detector.

The components to be evaluated in the method of the present invention are described in detail in the following specification.

An embodiment of the present method 100 is illustrated in FIG. 1. The present method will be described in more detail with reference to FIG. 1 as follows:

Step (a): Providing an Amplification Composition Comprising a Pair of Dimer-Forming Primers 110

First, an amplification composition is prepared for performing the amplification reaction of step (b) 110. The amplification composition used to carry out the method of the present invention comprises a pair of dimer-forming primers.

A key feature of the present method is to use a pair of dimer-forming primers having a unique structure.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. Particularly, the primer is a single-stranded deoxyribonucleotide molecule. The primer used in this invention may comprise a naturally occurring dNMP (i.e., dAMP, dGMP, dCMP and dTMP), a modified nucleotide, or a non-natural nucleotide. The primer may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term "dimer-forming primer" (herein abbreviated as "DPF") as used herein refers to a primer that can be partially hybridized with another dimer-forming primer other than a template under certain conditions and can be extended by the polymerization activity of a nucleic acid polymerase.

The term "pair of dimer-forming primers" or "dimer-forming primer pair" as used herein refers to a pair of two primers, e.g., a first primer and a second primer, which can be partially hybridized to each other and can each be extended by the polymerization activity of a nucleic acid polymerase.

The term "annealing" or "priming" in the context of the dimer-forming primer refers to the apposition of a 3'-dimer-forming portion of the first primer to a 3'-dimer-forming portion of the second primer, whereby the apposition enables the polymerase to polymerize nucleotides into a nucleic acid molecule which is complementary to a 5'-templating portion or a part thereof.

A conventional primer hybridizes to a nucleic acid strand (template) to be amplified, whereas the dimer-forming primer of the present invention hybridizes to another dimer-forming primer to be amplified.

Primer dimers are well known to those of skill in the art. Primer dimers are potential byproducts in nucleic acid amplification reactions such as PCR. Primer dimers may inhibit the amplification of a target nucleic acid sequence in an amplification reaction and interfere with accurate analysis. Conventional techniques have focused on inhibiting the formation of such primer dimers. However, to our knowledge, there is no known prior art that discloses the utility of artificial primer dimers.

The pair of dimer-forming primers used in the method of the present invention has the following characteristics:
(i) It comprises a first primer and a second primer;
(ii) The first primer and the second primer each comprise a 3'-dimer-forming portion; and
(iii) The nucleotide sequence of the 3'-dimer-forming portion in the first primer is complementary to the nucleotide sequence of the 3'-dimer-forming portion in the second primer.

The pair of dimer-forming primers of the present invention comprises two primers, a first primer and a second primer. In one embodiment of the present invention, the pair of dimer-forming primers consists of a first primer and a second primer.

The terms "first primer" and "second primer" as used herein are intended to specify two distinct primers. It is to be understood that the terms do not indicate a specific primer and does not confer any particular order, meaning, preference, etc. between the primers. Also, unless otherwise stated, the first primer and the second primer may be used interchangeably with the first dimer-forming primer and the second dimer-forming primer.

In the pair of dimer-forming primers of the present invention, the first primer and the second primer each comprises a 3'-dimer-forming portion.

The term "3'-dimer forming portion" as used herein refers to a portion which is located at the 3'-end part of a dimer-forming primer and can be hybridized with a 3'-dimer portion of another dimer-forming primer under certain hybridization conditions to form a dimer. In other words, the 3'-dimer forming portion refers to a 3'-end part of a dimer-forming primer, which has a nucleotide sequence that can hybridize with a 3'-dimer forming portion of another dimer-forming primer.

The term "hybridizing" as used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization between two dimer-forming primers may be carried out under suitable hybridization conditions routinely determined by optimization procedures. Conditions such as temperature, concentration of components, hybridization and washing times, buffer components, and their pH and ionic strength may be varied depending on various factors, including the length and GC content of the dimer-forming primers. For instance, when a pair of dimer-forming primers having relatively short dimer-forming portions is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

According to the present invention, the first primer has a 3'-dimer-forming portion at the 3'-end part; the second primer has a 3'-dimer-forming portion at the 3'-end part; and a nucleotide sequence of the 3'-dimer-forming portion in the first primer is complementary to a nucleotide sequence of the 3'-dimer-forming portion in the second primer.

The term "complementary" or "complementarity" in the context of the 3'-dimer-forming portions of the first primer and the second primer is used herein to mean that the 3'-dimer-forming portion in the first primer is sufficiently complementary to hybridize selectively to the 3'-dimer-forming portion in the second primer under the designated annealing conditions or stringent conditions, encompassing the terms "substantially complementary" and "perfectly complementary", preferably perfectly complementary.

In an embodiment of the present invention, the 3'-dimer-forming portions of the first primer and the second primer have nucleotide sequences substantially complementary to each other.

According to an embodiment of the present invention, the 3'-dimer-forming portions of the first primer and the second primer each have one or more non-complementary nucleotides, so long as the non-complementary nucleotides does not significantly affect hybridization between the 3'-dimer-forming portions and extension at 3'-end of the primers. For example, the 3'-dimer-forming portions of the first primer and the second primer each may have 5, 4, 3, 2 or 1 non-complementary nucleotides depending upon its length. The first primer and the second primer can be successfully hybridized and extended depending on the reaction conditions even in the presence of some mismatch nucleotides (e.g., 1-5 mismatch nucleotides) in the 3'-dimer-forming portions.

The non-complementary nucleotides may or may not be consecutive in the 3'-dimer-forming portions.

According to an embodiment of the present invention, the 3'-dimer-forming portions of the first primer and the second primer each have at least 2, at least 3, at least 4, at least 5, at least 6, at least 7, or at least 8 consecutive complementary nucleotides, including a nucleotide at the 3'-terminus.

According to one embodiment of the present invention, the 3'-dimer-forming portions of the first primer and the second primer have nucleotide sequences perfectly complementary to each other.

The 3'-dimer forming portions of the first primer and the second primer each are 3 to 50 nucleotides in length. In an embodiment of the present invention, the 3'-dimer-forming portions of the first primer and the second primer each are 3, 4, 5, 6, 7, 8, 9, 10, 11, 12, 13, 14, 15, 16, 17, 18, 19, 20, 21, 22, 23, 24, 25, 30, 40 or 50 nucleotides in length. For example, the 3'-dimer-forming portions of the first and second primers each are 3-50, 3-40, 3-35, 3-30, 3-25, 3-20, 3-17, 3-15, 3-12, 3-10, 3-9, 3-8, 3-7, 3-6, 3-5, 3-4, 4-50, 4-40, 4-35, 4-30, 4-25, 4-20, 4-17, 4-15, 4-12, 4-10, 4-9, 4-8, 4-7, 4-6, 4-5, 5-50, 5-40, 5-35, 5-30, 5-25, 5-20, 5-17, 5-15, 5-12, 5-10, 5-9, 5-8, 5-7, 5-6, 6-50, 6-40, 6-35, 6-30, 6-25, 6-20, 6-17, 6-15, 6-14, 6-13, 6-12, 6-11, 6-10, 6-9, 6-8, 6-7, 7-50, 7-40, 7-35, 7-30, 7-25, 7-20, 7-19, 7-18, 7-17, 7-16, 7-15, 7-14, 7-13, 7-12, 7-11, 7-10, 7-9, 7-8, 8-50, 8-40, 8-35, 8-30, 8-25, 8-20, 8-17, 8-15, 8-12, 8-10, 8-9, 9-50, 9-40, 9-35, 9-30, 9-25, 9-20, 9-17, 9-15, 9-12, 9-10, 10-50, 10-40, 10-35, 10-30, 10-25, 10-20, 10-17, 10-15, 10-12, 12-50, 12-40, 12-35, 12-30, 12-25, 12-20, 12-17, 12-15, 15-50, 15-40, 15-35, 15-30, 15-25, 15-20, 15-17 or 17-20 nucleotides in length. In a particular embodiment, the 3'-dimer-forming portions of the first primer and the second primer each are 5 nucleotides, 6 nucleotides, 7 nucleotides, 8 nucleotides, 9 nucleotides or 10 nucleotides in length.

The length of the 3'-dimer-forming portions of the first primer and the second primer as described above indicates a range from a nucleotide at the 3'-end (including the nucleotide at the 3'-terminus) to a specific nucleotide in the 5' direction. For example, if the 3'-dimer-forming portion is 5 nucleotides in length, the 3'-dimer-forming portion ranges from the $1^{st}$ nucleotide at the 3'-end to the $5^{th}$ nucleotide (including the $1^{st}$ and $5^{th}$ nucleotides).

In one embodiment of the present invention, each of the first primer and the second primer consists of two portions: (i) a 5'-templating portion; and (ii) a 3'-dimer-forming portion.

The term "5'-templating portion" of a dimer-forming primer as used herein refers to the remaining portion (region) at the 5'-end part of the primer, except for the 3'-dimer-forming portion. The term "5'-templating portion" of a dimer-forming primer also refers to a portion of a dimer-forming primer, serving as a template for extension of another dimer-forming primer hybridized to the dimer-forming primer. The 5'-templating portion of a dimer-forming primer has a nucleotide sequence that is non-complementary to the 3'-dimer-forming portion of another dimer-forming primer.

The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", preferably perfectly non-complementary. For example, the term "non-complementary" with reference to the 5'-templating portion of a dimer-forming primer mean that the 5'-templating portion of a dimer-forming primer is sufficiently non-complementary not to hybridize selectively to the complete sequence of another dimer-forming primer under the designated annealing conditions or stringent conditions, encompassing the terms "substantially non-complementary" and "perfectly non-complementary", preferably perfectly non-complementary.

The 5'-templating portion of a dimer-forming primer according to the present invention may or may not have a self-complementary sequence. If the 5'-templating portion of a dimer-forming primer of the present invention has a self-complementary sequence, the 5'-templating portion may form a secondary structure, such as a hairpin-stem structure and may have a label for providing detectable signal (see Nazarenko et al, 2516-2521 Nucleic Acids Research, 1997, v. 25 no. 12, and U.S. Pat. No. 6,117,635, for Sunrise primer; Whitcombe et al, 804-807, Nature Biotechnology v. 17 AUGUST 1999 and U.S. Pat. No. 6,326, 145, for Scorpion primer).

The 5'-templating portion of the first primer may be any sequence as long as it has a non-complementary sequence to the 3'-dimer-forming portion of the second primer. Likewise, the 5'-templating portion of the second primer may be any sequence as long as it has a non-complementary sequence to the 3'-dimer-forming portion of the first primer.

The 5'-templating portions of the first primer and the second primer each are 4 to 100 nucleotides in length. In a particular embodiment, the lengths of the 5'-templating portions of the first primer and the second primer each ranges from at least 4, 10, 20, 30, 40, 60 or 80 nucleotides to no more than 100, 80, 70, 60, 50, 40, 35, 30, 25, 20, 15 or 10 nucleotides.

The dimer-forming primer according to the present invention should not be blocked at the 3'-end to be extended for amplification.

A dimer-forming primer according to the present invention can have three functions as a primer, a probe and a template, unlike conventional primers.

First, a dimer-forming primer of the present invention can serve as a primer by hybridizing to another dimer-forming primer and being extended. Second, a dimer-forming primer of the present invention can serve as a probe by providing a signal from a label upon formation of the dimer, upon melting of the dimer, or upon melting followed by hybridization. Third, a dimer-forming primer of the present invention can serve as a template for hybridization with another dimer-forming primer and then extension. Therefore, when a dimer-forming primer according to the present invention is used in an amplification reaction, no additional templates, primers and probes may be required. In particular, the method of the present invention is carried out in the absence of a template specific for a dimer-forming primer, i.e., a template that hybridizes with a dimer-forming primer.

Meanwhile, the extension products, which are formed by the hybridization between and the extension of the first primer and the second primer, may serve as internally generated templates. In this case, the first primer or the second primer as a primer is specifically hybridized to the extension products, resulting in amplification of the internally generated template.

This indicates that the amplification reaction using the first primer and the second primer of the present invention can simulate a conventional amplification reaction, even without a template provided externally. Therefore, the amplification reaction using the first dimer-forming primer and the second dimer-forming primer of the present invention can be used to evaluate the performance or activity of the components involved in the reaction.

The first primer and the second primer, constituting the pair of dimer-forming primers of the present invention, do not require any specific length. In one embodiment, the first primer and the second primer each are 7 to 100 nucleotides in length. In a particular embodiment, the lengths of the first primer and the second primer ranges from at least 7, 10, 15, 20, 30, 40, 60 or 80 nucleotides to no more than 100, 80, 70, 60, 50, 40, 35, 30, 25, 20, 15 or 10 nucleotides. For example, the first primer and the second primer each may be 7-40, 7-60, 7-80, 7-100, 10-40, 10-60, 10-80, 10-100, 15-40, 15-60, 15-80, 15-100, 20-40, 20-60, 20-80, 20-100, 30-40, 30-60, 30-80 or 30-100 nucleotides in length.

A dimer-forming primer of the present invention may or may not have a self-complementary sequence. Where a dimer-forming primer of the present invention has a self-complementary sequence, it may form a secondary structure, such as a hairpin-stem structure by hybridization of the self-complementary sequence. According to one embodiment of the present invention, the sequences involved in forming a stem structure are both present in the 5'-templating portion or in the 3'-dimer-forming portion; one is present in the 5'-templating portion and the other is present in the 3'-dimer forming portion; or one is present in either the 5'-templating portion or the 3'-dimer forming portion and the other is present in a region spanning from a part of the 5'-templating portion to a part of the 3'-dimer forming portion. In one embodiment of the invention, each sequence involved in forming a stem structure comprises at least 3, at least 4, or at least 5 nucleotides, particularly in consecutive arrangement. In one embodiment of the invention, each sequence involved in forming a stem structure comprises no more than 15, no more than 10, no more than 8 nucleotides, particularly in consecutive arrangement.

Where a dimer-forming primer of the present invention does not have a self-complementary sequence, the dimer-forming primer may form a random-coil.

The first primer and the second primer constituting the pair of dimer-forming primers may be comprised of naturally occurring dNMPs. Alternatively, the first primer and the second primer may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The first primer and the second primer may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

The modified nucleotides, non-natural nucleotides or universal bases may or may not be present consecutively in a dimer-forming primer. The modified nucleotides, non-natural nucleotides or universal bases may be 1-8, 1-5, 1-3 or 1-2 nucleotides. The modified nucleotides, non-natural nucleotides or universal bases may be at any position within a dimer-forming primer. In one embodiment of the invention, the modified nucleotides, non-natural nucleotides or universal bases may be located in the 5'-templating portion, in the 3'-dimer-forming portion, or both. The sequences located on the left side and the right side of the modified nucleotide or non-natural nucleotide or universal base may be complementary to each other and hybridize to each other to form a stem structure.

A dimer-forming primer of the present invention may comprise any additional sequence in addition to the 5'-templating portion and the 3'-dimer-forming portion. According to an embodiment of the present invention, the additional sequence is located in the 5' direction to the 5'-templating portion and does not serve as a template and does not hybridize with another dimer-forming primer. The additional sequence included in a dimer-forming primer may comprise a blocker to prevent extension of another dimer-forming primer.

The first primer and/or the second primer constituting the pair of the dimer-forming primers according to the present invention may comprise a label system suitable for a selected signaling mode.

The signaling mode and the label system for the first primer and/or the second primer are described in detail in step (b).

In step (a) of the present method, there is provided an amplification composition comprising a pair of dimer-forming primers.

The term "amplification composition" or "composition for amplification reaction" as used herein refers to a collection or mixture of chemical components used in an amplification reaction. In particular, the term refers to a collection or mixture of chemical components involved in the extension of a pair of dimer-forming primers or the signal generation therefrom, including the pair of dimer-forming primers. It is noted that the term is intended to exclude any physical or mechanical components used in an amplification reaction, e.g., a vessel, a thermocycler, or a detector.

As described above, the amplification composition comprises one or more components, including a pair of dimer-forming primers.

Examples of the components that can be included in the amplification composition are a nucleic acid polymerase, dNTPs, a buffer, a salt, an additive, a label, or the like.

The components that can be included in the amplification are described below:

(a) Nucleic Acid Polymerase

The amplification composition may contain a nucleic acid polymerase to extend the primer. The nucleic acid polymerase may be a template-dependent nucleic acid polymerase. The template-dependent nucleic acid polymerase may include any nucleic acid polymerases, for example, Klenow fragment of *E. coli* DNA polymerase I, a thermostable DNA polymerase and bacteriophage 17 DNA polymerase.

(b) dNTPs

The amplification composition may contain dNTPs, building blocks of DNA or RNA to be synthesized. The dNTPs include a mixture of four deoxyribonucleotides, i.e., dATP, dCTP, dGTP, and dTTP (or dUTP).

(c) Buffer

The amplification composition may contain a buffer to provide a pH environment for optimal activity of a nucleic acid polymerase and to prevent rapid changes in pH due to temperature change and chemical action during amplification reaction. Examples of a buffer include Tris-HCl.

(d) Salt

The amplification composition may contain a salt to help stabilize the activity of nucleic acid polymerase. The salt may be a salt of magnesium or potassium, for example $MgCl_2$, $MgSO_4$ or KCl. The salt may be added at various concentrations known in the art.

(e) Additive

The amplification composition may contain various additives to stabilize a nucleic acid polymerase. Examples of the additives include BSA, DMSO, betaine, KCl, non-ionic surfactants (e.g., Tween 20, Triton X-100).

(f) Label

The amplification composition may contain a label to generate a signal. Details of the label are described elsewhere in the present specification.

It is to be understood that the amplification composition of the present invention may further comprise, in addition to the above-mentioned components, any other components known in the art.

In one embodiment, the amplification composition further comprises a sample which contains or is suspected of containing a target nucleic acid sequence. In general, a sample may contain any substance that lowers the efficiency of amplification reaction (e.g., any substance that degrades components or inhibits its performance). Thus, a sample may be included in the amplification composition of the present invention to determine whether the sample contains such an inhibitor, i.e., to evaluate the performance of the sample. When the sample is included in the amplification composition, the pair of dimer-forming primers according to the present invention may serve as an internal control.

The sample contained in the amplification composition may be a sample before extracting a target nucleic acid sequence in the sample or a sample after extracting a target nucleic acid sequence in the sample.

The pair of dimer-forming primers can serve as an internal control for monitoring a nucleic acid extraction process or an amplification reaction.

In an embodiment, the pair of dimer-forming primers is spiked into a sample, the spiked sample is subjected to the nucleic acid extraction process, and the extraction product is aliquoted into the amplification composition. In an embodiment, the pair of dimer-forming primers is added into the amplification composition directly, particularly together with other oligonucleotides including primers for target nucleic acid.

Each component in the amplification composition can be evaluated for its performance by the method of the present invention and therefore can be regarded as a component to be evaluated by the method of the invention. However, a pair of dimer-forming primers is not regarded as a component to be evaluated by the methods of the present invention, although it is a component contained in the amplification composition.

Step (b): Subjecting the Amplification Composition to an Amplification Reaction in an Amplification Device 120

Next, the amplification composition of step (a) is subjected to an amplification reaction in an amplification device 120. In the amplification reaction, the first primer and the second primer form a dimer through hybridization between the 3'-dimer-forming portions under amplification conditions, and are each extended by a nucleic acid polymerase to form an extended duplex; wherein a detectable signal is provided in a dependent manner on the presence of the extended duplex.

The term "amplification conditions" as used herein refers to conditions such as the presence of components necessary for amplification, and suitable temperature and pH. The term "amplification conditions" as used herein refers to conditions for separate steps included in an amplification reaction such as annealing/hybridization of oligonucleotides, extension of primers and denaturation of duplex. Such conditions may be varied depending upon various factors, including the length and GC contents of dimer-forming primers and the length and GC contents of dimer-forming portion. The detailed conditions can be found in Joseph Sambrook et al., Molecular Cloning, A Laboratory Manual, Cold Spring Harbor Laboratory Press, Cold Spring Harbor, N.Y. (2001); and M. L. M. Anderson, Nucleic Acid Hybridization, Springer-Verlag New York Inc. N.Y. (1999).

The expression "a detectable signal is provided in a dependent manner on the presence of the extended duplex" as used herein is intended to mean that a detectable signal is provided directly or indirectly from the presence of the extended duplex. In particular, the detectable signal may be provided from the extended duplex per se, or may be provided from other oligonucleotides associated with the extended duplex.

Figure 2:
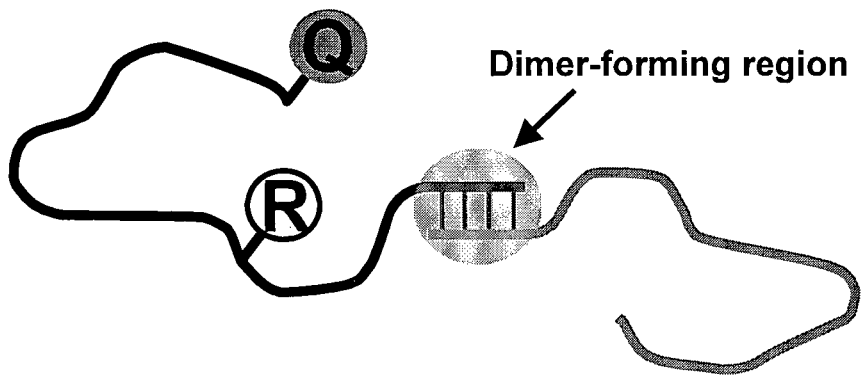
FIG. 2 shows an embodiment of a process in which a signal is generated by a pair of dimer-forming primers. According to the method of the present invention, two primers forms a dimer through hybridization between 3'-dimer-forming portions, and then are each extended to form an extended duplex, thereby generating a signal.
Figure 2:
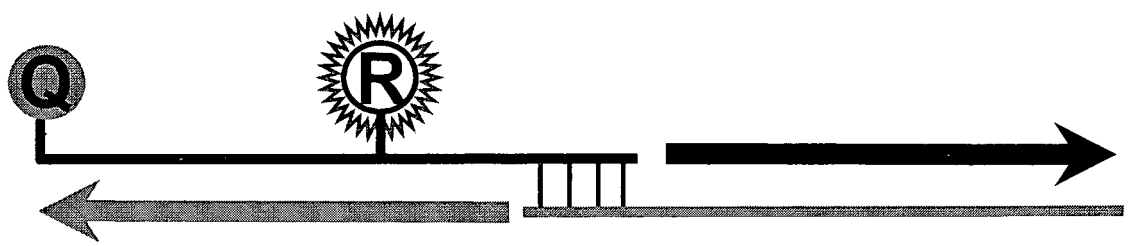

The amplification reaction in step (b) comprises (i) hybridization of a pair of dimer-forming primers; and (ii) extension of each dimer-forming primer. The amplification reaction is illustrated in FIG. 2.

(i) Hybridization of a Pair of Dimer-Forming Primers

A pair of dimer-forming primers is hybridized to each other. Specifically, the first primer and the second primer are hybridized to each other by complementarity between the 3'-dimer-forming portions, thereby forming a dimer.

According to one embodiment, the first primer and the second primer each comprise in a 5' to 3' direction (i) a 5'-templating portion and (ii) a 3'-dimer-forming portion. In the hybridization process, the 3'-dimer-forming portion is involved in hybridization, but the 5'-templating portion is not involved in hybridization. In particular, hybridization occurs between the 3'-dimer-forming portions of the two primers (see FIG. 2(i)).

Typically, hybridization between the two primers can generate a various types of dimers. These dimers can be divided into three categories depending on whether each primer is extended or not:

(a) a dimeric form in which both the first primer and the second primer can be extended;

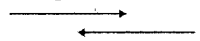

(b) a dimeric form in which only one of the first primer and the second primer can be extended; and

 or (c) a dimeric form in which neither the first primer nor the second primer can be extended

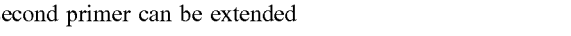, , or

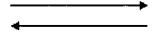.

Of the three dimeric forms above, contemplated by the hybridization of the present invention is a dimeric form (a) in which both the first primer and the second primer can be extended. However, it should be understood that the method of the present invention does not exclude the formation of the dimeric forms (b) and (c).

Dimeric forms contemplated by the methods of the present invention include those in which the first primer and the second primer are partially hybridized (partially overlapped) through the 3'-dimer-forming portions of the two primers. Such dimeric form is referred to as a partial dimer. Each primer of the partial dimer may be extended by the polymerization activity of a nucleic acid polymerase.

In one embodiment, a dimer formed by partial hybridization between the first primer and the second primer has a distinct tripartite structure consisting of: (i) a single-stranded portion composed of the first primer; (ii) a double-stranded portion composed of the first primer and the second primer; and (iii) a single-stranded portion composed of the second primer.

The hybridization of the pair of dimer-forming primers as described above can be carried out under conditions in which hybridization of the first primer and the second primer is possible.

In particular, the hybridization conditions can be adjusted appropriately in consideration of each primer designed and synthesized in accordance with the dimeric form contemplated.

(ii) Extension of the Pair of Dimer-Forming Primers

The first primer and the second primer of the dimer are each extended by a nucleic add polymerase to form an extended duplex.

The term "extended duplex" or "extended dimer" as used herein means a duplex formed by extension reaction in which the first primer is extended along the 5'-templating portion of the second primer by a template-dependent nucleic acid polymerase and the second primer is extended along the 5'-templating portion of the first primer by a template-dependent nucleic acid polymerase.

Each extension product of primers may be expressed as an extended strand. A portion of the extended strand except the primers which is a newly extended sequence may be expressed as an extended sequence.

The template-dependent nucleic acid polymerase used in the step (b) may include any nucleic acid polymerases, for example, Klenow fragment of *E. coli* DNA polymerase I, a thermostable DNA polymerase and bacteriophage T7 DNA polymerase. In particular, the polymerase is a thermostable DNA polymerase which may be obtained from a variety of bacterial species, including *Thermus aquaticus* (Taq), *Thermus thermophilus* (Tth), *Thermus filiformis, Thermis flavus, Thermococcus literalis, Thermus antranikianii, Thermus caldophilus, Thermus chliarophilus, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosiphoafricanus, Pyrococcus furiosus* (Pfu), *Pyrococcus woesei, Pyrococcus horikoshii, Pyrococcus abyssi; Pyrodictium occultum, Aquifex pyrophilus* and *Aquifex aeolieus*.

The extension of the dimer may be adjusted appropriately in consideration of the optimum temperature for the activity of the nucleic acid polymerase and the like.

According to one embodiment of the present invention, the amplification reaction of step (b) can be carried out under amplification conditions conventionally known in the art.

According to one embodiment of the present invention, the amplification reaction of step (b) can be carried out under PCR conditions conventionally known in the art.

According to one embodiment of the present invention, the amplification reaction of step (b) may further comprise a denaturation step, and in this case, denaturation, hybridization and extension steps can be repeated.

The denaturation step is performed in consideration of an appropriate temperature and time for dissociating the first primer and the second primer, or an extended duplex thereof. The hybridization step is performed in consideration of an appropriate temperature and time for hybridizing the first primer to the second primer or for hybridizing the first primer to the second primer to the strands of the extended duplex. The extension step is performed in consideration of an appropriate temperature and time for extending the first primer and the second primer.

The detailed conditions for denaturation, hybridization and extension can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

According to the present invention, the amplification reaction further comprises denaturing the extended duplex, hybridizing denatured strands with the first primer and the second primer, and extending the first primer and the second primer to form the extended duplex.

The extension products which are formed by the hybridization between and the extension of the first primer and the second primer may serve as internally generated templates. In this case, the first primer or the second primer as a primer is specifically hybridized to the extension products, resulting in amplification of the internally generated template.

In the method of the present invention, the amplification reaction of step (b) is carried out in an amplification device.

The term "amplification device" as used herein is intended to encompass all physical or mechanical components used in an amplification reaction. Specifically, the amplification device encompasses amplification vessels as well as thermocyclers and detectors. The expression "an amplification reaction is carried out in an amplification device" as used herein means that an amplification composition is subjected to an amplification reaction using an amplification vessel, a thermocycler, and a detector.

In one embodiment of the present invention, the component in the amplification device is a thermocycler. In another embodiment of the present invention, the component in the amplification device is a detector. In still another embodiment of the present invention, the component in the amplification device is a vessel. The components may or may not be coupled to each other.

The thermocycler and/or the detector are well known in the art, including, without limitation, CFX (Bio-Rad), iCycler (Bio-Rad), LightCycler (Roche), StepOne (ABI), 7500 (ABI), ViiA7 (ABI), QuantStudio (ABI), AriaMx (Agilent).

The vessel is well known in the art, including a tube, a strip, a plate, and the like.

Each component in the amplification device can be evaluated for its performance by the method of the present invention and therefore can be regarded as a component to be evaluated by the method of the invention.

In step (b) of the method of the present invention, a detectable signal is provided in a dependent manner on the presence of the extended duplex.

The term "signal" as used herein means any signal capable of indicating the presence or absence of the extended duplex. For example, the signal includes a signal from labels (signal generation or extinguishment), a signal change from labels (signal increase or decrease), a melting curve, a melting pattern and a melting temperature (or $T_m$ value).

The detectable signal may be generated by a label(s) or labeling system.

The detectable signal may be generated by using various signal-generating means (i.e. labeling system) well known in the art.

In an embodiment, the detectable signal is generated in a dependent manner on the presence of the extended duplex, without using an additional oligonucleotide.

In another embodiment, the detectable signal is generated in a dependent manner on the presence of the extended duplex, by using an additional oligonucleotide.

In particular, the detectable signal is provided by (i) at least one label linked to the first primer and/or the second primer, (ii) a label incorporated into the extended duplex during the extension, (iii) a label incorporated into the extended duplex during the extension and a label linked to the first primer and/or the second primer, (iv) an intercalating label; or (v) at least one label linked to a detection oligonucleotide. Furthermore, the detection oligonucleotide as described above can provides a signal indicative of the presence of the extended duplex from the label of the detection oligonucleotide with or without the aid of other additional oligonucleotides such as a mediation oligonucleotide.

The label systems useful in this invention will be described in detail as follows:

(i) At Least One Label Linked to the First Primer and/or the Second Primer

According to one embodiment, the signal is provided by at least one label linked to the first primer and/or the second primer. The label of the first primer or the second primer can provide a detectable signal in real time upon formation of the extended duplex, or it can provide a detectable signal upon melting of the extended duplex or upon hybridization after the melting.

According to one embodiment, the signal can be provided in the hybridization step of the first primer and the second primer, depending upon the position of the label. In this case, the extended duplex has different Tm value from that of the dimer, and thus the difference in Tm values of the extended duplex and the dimer permits to discriminate the signal of the extended duplex from the signal of the dimer. For example, when detecting a signal at a predetermined temperature such as real-time detection, the signal is detected at a temperature at which the dimer of the first primer and the second primer is substantially dissociated, but the extended duplex is not substantially dissociated. Alternatively, the presence of the extended duplex can be determined by measuring the Tm of the resultant.

According to one embodiment, the label is not linked to the 3'-end of the dimer-forming primer so as not to interfere with extension of the primer.

The label includes an interactive dual label and a single label.

(i-1) Interactive Dual Label (a) Intrastrand Interactive Dual Label

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The donor molecule and the acceptor molecule may be described as a reporter molecular and a quencher molecule in the present invention, respectively. Interactive dual label includes the label pair providing detectable signal based on contact-mediated quenching (Salvatore et al., Nucleic Acids Research, 2002 (30) no.21 e122 and Johansson et al., J. AM. CHEM. SOC 2002 (124) pp 6950-6956). In the present invention, the interactive label system includes any or all cases inducing signal changes by interaction between at least two molecules (e.g. dyes).

Particularly, the signal indicative of the presence of the extended strand is generated by interactive label systems, more preferably the FRET label system (i.e., interactive dual label system).

In an embodiment of an interactive dual label system, the 5'-templating portion of the first primer has a reporter molecule and a quencher molecule. The first primer and the second primer form a dimer through hybridization between the 3'-dimer-forming portions, and are each extended to form an extended duplex. Before the extended duplex is formed, i.e., before the first primer is hybridized with the second primer, or before the first primer and the second primer of the dimer are extended, the reporter molecule and the quencher molecule are conformationally adjacent to each other to allow the quencher molecule to quench the signal from the reporter molecule. In contrast, when the extended duplex is formed, the reporter molecule and the quencher molecule are conformationally separated to allow the quencher molecule to unquench the signal from the reporter molecule, giving rise to changes in signals from the interactive dual label. Thus, such signal change indicates the formation and presence of the extended duplex, and the formation and presence of the extended duplex indicates amplification of the dimer-forming primers.

When the extended dimer is dissociated, the reporter molecules and the quencher molecules are conformationally adjacent to each other to allow the quencher molecule to quench the signal from the reporter molecule, giving a signal. Thus, when the interactive dual label system is used, the signal can be detected by melting or hybridization after the melting.

In an embodiment of an interactive dual label system, the 5'-templating portion of the first primer has one of a reporter molecule and a quencher molecule and the 3'-dimer-forming portion has the other of the reporter molecule and the quencher molecule. Before the extended duplex is formed, the reporter molecule and the quencher molecule are conformationally adjacent to each other to allow the quencher molecule to quench the signal from the reporter molecule. However, when the extended duplex is formed, the reporter molecule and the quencher molecule on the first primer are conformationally separated to allow the quencher molecule to unquench the signal from the reporter molecule, giving rise to changes in signals from the interactive dual label.

The expression "the reporter molecule and the quencher molecule are conformationally adjacent" as used herein means that the reporter molecule and the quencher molecule are three-dimensionally adjacent to each other by a conformational structure of the first primer or the second primer such as random coil and hairpin structure.

The expression "the reporter molecule and the quencher molecule are conformationally separated" as used herein means that the reporter molecule and the quencher molecule are three-dimensionally separated by change of a conformational structure upon the formation of the extended duplex.

In an embodiment of the present invention, the label may be linked to any site on the first primer or the second primer, so long as the signal from the label is unquenched by the formation of the extended duplex.

In an embodiment of the present invention, both the reporter molecule and the quencher molecule are linked to the 3'-dimer-forming portion of the first primer or the second primer. As described above, when the 3'-dimer-forming portion of the first primer or the second primer is labelled with a dual label, the hybridization between the first primer and the second primer can provide a signal. In this labeling system, the extended duplex has different Tm value from that of the dimer, and thus the difference in Tm values of the extended duplex and the dimer permits to discriminate the signal of the extended duplex from the signal of the dimer.

According to an embodiment of the present invention, one of the reporter molecule and the quencher molecule on the first primer is located at its 5'-end or at 1-5 nucleotides apart from its 5'-end and the other is located to quench and unquench the signal from the reporter molecule depending on conformation of the first primer.

According to an embodiment of the present invention, one of the reporter molecule and the quencher molecule on the first primer is located at its 3'-end or at 1-5 nucleotides apart from its 3'-end and the other is located to quench and unquench the signal from the reporter molecule depending on conformation of the first primer.

According to an embodiment of the present invention, the reporter molecule and the quencher molecule are positioned no more than 80 nucleotides, no more than 60 nucleotides, no more than 30 nucleotides, no more than 25 nucleotides, or no more than 20 nucleotides apart from each other. According to an embodiment, the reporter molecule and the quencher molecule are positioned at least 4 nucleotides, at least 6 nucleotides, at least 8 nucleotides, at least 10 nucleotides, at least 12 nucleotides, at least 15 nucleotides, or at least 17 nucleotides apart from each other.

According to an embodiment of the present invention, each of the first primer and the second primer may have the same or different combination of dual labels.

(b) Interstrand Interactive Dual Label

In an embodiment, the first primer has one of an interactive dual label comprising a reporter molecule and a quencher molecule and the second primer has the other of the interactive dual label.

For example, the first primer has a reporter molecule at the 3'-dimer-forming portion and the second primer has a quencher molecule at the 3'-dimer-forming portion. Signal quenching does not occur before hybridization between the first primer and the second primer, but when hybridized, the reporter molecule and the quencher molecule are adjacent to each other to allow the quencher molecule to quench the signal from the reporter molecule. In this labeling system, the extended duplex has different Tm value from that of the dimer, and thus the difference in Tm values of the extended duplex and the dimer permits to discriminate the signal of the extended duplex from the signal of the dimer. In addition, when the extended dimer is melted, the reporter molecules and the quencher molecules are separated from each other to allow the quencher molecule to unquench the signal from the reporter molecule, giving rise to changes in signals from the interactive dual label. The signal can be provided in hybridization after the melting.

The reporter molecule and the quencher molecule may be located at any site of the first primer and the second primer, so long as the signal from the reporter molecule is quenched upon hybridization between the first primer and the second primer.

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996); U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention. Examples of those are BHQ and DABCYL.

In the FRET label adopted to the first primer or the second primer, the reporter encompasses a donor of FRET and the quencher encompasses the other partner (acceptor) of FRET. For example, a fluorescein dye is used as the reporter and a rhodamine dye as the quencher.

(i-2) Single Label

The present invention is also excellently executed using single label systems for providing signal changes upon formation of the extended duplex, upon melting, or upon hybridization after the melting.

According to an embodiment, the first primer or the second primer has a single label, and the formation of the extended duplex in the step (b) induces change of a signal from the single label to give the target signal.

According to an embodiment of single label systems, the 5'-templating portion of the first primer has a single fluorescent label. The first primer and the second primer form a dimer through hybridization between the 3'-dimer-forming portions, and are extended to an extended duplex. Before the extended duplex is formed, i.e., before the first primer is hybridized with the second primer, or before the first primer and the second primer of the dimer is extended, the fluorescent intensity from the single fluorescent label becomes decreased; whereas by the formation of the extended duplex, the fluorescent intensity from the single fluorescent label becomes increased, such that the signal is given to indicate the presence of the extended duplex. Alternatively, when the extended duplex is melted, the signal intensity from the single fluorescent label becomes decreased, such that the signal is given to indicate the presence of the extended duplex.

According to an embodiment, the single label may be located at any site on the first primer, so long as the signal level from the single label is changed depending on the formation of the extended duplex.

According to an embodiment, the single label is linked to the 3'-dimer-forming portion of the first primer. Where the 3'-dimer-forming portion is labelled with a single label, the dimer between the first primer and the second primer can provide a signal. In this label system, the extended duplex has different Tm value from that of the dimer, and thus the difference in Tm values of the extended duplex and the dimer permits to discriminate the signal of the extended duplex from the signal of the dimer.

According to an embodiment, each of the first primer and the second primer may have the same or different single label.

The single label used herein has to be capable of providing a different signal depending on its presence on a double strand or single strand. The single label includes a fluorescent label, a luminescent label, a chemiluminescent label, an electrochemical label and a metal label. Particularly, the single label includes a fluorescent label.

The types and preferable binding sites of single fluorescent labels used in this invention are disclosed U.S. Pat. Nos. 7,537,886 and 7,348,141, the teachings of which are incorporated herein by reference in their entirety. Particularly, the single fluorescent label includes JOE, FAM, TAMRA, ROX and fluorescein-based label. The labeled nucleotide residue is preferably positioned at internal nucleotide residue within the oligonucleotide rather than at the 5'-end or the 3'-end.

The single fluorescent label useful in the present invention may be described with reference to descriptions for reporter and quencher molecules as indicated above.

(ii) Label Incorporated into the Extended Duplex

The present invention may employ a label incorporated into the extended duplex during the extension reaction for providing the target signal upon formation of the extended duplex, upon melting, or upon hybridization after the melting.

Although the first primer and the second primer have no label, a label incorporated into the extended duplex during the extension reaction is successfully used to allow the extended duplex to be labeled.

According to an embodiment, the signal is provided by a single label incorporated into the extended duplex during the extension reaction; wherein the incorporated single label is linked to a nucleotide incorporated during the extension reaction; wherein the formation of the extended duplex in the step (b) induces change of a signal from the single label to give the target signal or the melting of the extended duplex in the step (b) induces change of a signal from the single label to give the target signal.

According to an embodiment, a nucleotide incorporated during the extension reaction has a first non-natural base and the first primer has a nucleotide having a second non-natural base with a specific binding affinity to the first non-natural base. The nucleotide having the second non-natural base may be located at any site on the templating portion of the first primer.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432, 272, 5,965,364, 6,001,983, and 6,037,120. The base pairing between non-natural bases involves two or three hydrogen bonds as natural bases. The base pairing between non-natural bases is also formed in a specific manner.

Specific examples of non-natural bases include the following bases in base pair combinations: iso-C/iso-G, iso-dC/iso-dG, K/X, H/J, and M/N (see U.S. Pat. No. 7,422, 850).

The second primer is hybridized with the first primer with a nucleotide having a second non-natural base (e.g., iso-dC) with a specific binding affinity to a first non-natural base (e.g., iso-dG). The extension is carried out in the presence of a nucleotide having the first non-natural base labeled with a single fluorescent label, forming the extended duplex. In the extension reaction, the nucleotide having the first non-natural base is incorporated at an opposition site to the nucleotide having the second non-natural base.

(iii) Label Incorporated into the Extended Duplex and Label Linked to the First Primer and/or the Second Primer The present invention may employ a labeling system using cooperation of a label incorporated into the extended duplex during the extension reaction and a label linked to the first primer and/or the second primer.

According to an embodiment, the signal is provided by a label incorporated into the extended duplex during the extension reaction and a label linked to the first primer and/or the second primer, and the incorporated label is linked to a nucleotide incorporated during the extension reaction; wherein the two labels are an interactive dual label of a reporter molecule and a quencher molecule; wherein the formation of the extended duplex in the step (b) induces change of a signal from the interactive dual label to give the signal.

As one example, one label is linked to the first primer (particularly the 5'-templating portion of the first primer) and a nucleotide linked to the other label is incorporated into the extended strand of the second primer during the extension reaction of the second primer, thereby inducing change of a signal from the interactive dual label. As another example, one label is linked to the first primer (particularly the 3'-dimer-forming portion of the first primer) and a nucleotide linked to the other label is incorporated into the extended strand of the first primer during the extension reaction of the first primer, thereby inducing change of a signal from the interactive dual label.

The site of the label on the first primer and the incorporation site of the label incorporated are determined to the extent that the two labels are acted as an interactive dual label for inducing signal change.

More particularly, the nucleotide incorporated during the extension reaction has a first non-natural base and the primer acting as a template for the incorporated nucleotide has a nucleotide having a second non-natural base with a specific binding affinity to the first non-natural base.

As one example, the first primer (particularly, 5'-templating portion of the first primer) has one label of a reporter and quencher molecule and a nucleotide having a second non-natural base (e.g., iso-dC). The extension reaction is performed in the presence of a nucleotide having the other label and a first non-natural base (e.g., iso-dG) with a specific binding affinity to the second non-natural base in the first primer. In the extension reaction, the first primer is hybridized with the second primer and the second primer is extended, during which the nucleotide having the first non-natural base is incorporated at an opposition site to the nucleotide having the second non-natural base in the first primer. As a result, the signal from the reporter molecule is quenched by the quencher molecule to induce a signal change.

When the extended duplex is melted, the reporter molecule and the quencher molecule are separated to allow the quencher molecule to unquench the signal from the reporter molecule, such that the target signal is given to indicate the presence of the extended duplex.

As another example, the first primer (particularly, 3'-templating portion of the first primer) has one label of a reporter and quencher molecule and the 5'-templating portion of the second primer has a nucleotide having a second non-natural base (e.g., iso-dC). The extension reaction in the step (b) is performed in the presence of a nucleotide having the other label and a first non-natural base (e.g., iso-dG) with a specific binding affinity to the second non-natural base. In the extension reaction, the first primer is hybridized with the second primer and the first primer is extended, during which the nucleotide having the first non-natural base is incorporated at an opposition site to the nucleotide having the second non-natural base in the second primer. As a result, the signal from the reporter molecule is quenched by the quencher molecule to induce a signal change.

The site of the label on the first primer and the site of the nucleotide having second non-natural base in the first primer or the second primer are determined to the extent that a signal change can occur by interaction between the two labels upon incorporation of the other label.

(iv) Intercalating Label

The present invention may employ an intercalating label for providing the target signal indicative of the presence of the extended duplex.

Exemplified intercalating dyes useful in this invention include SYBR™ Green I, PO-PRO™-1, BO-PRO™-1, SYTO™ 43, SYTO™ 44, SYTO™ 45, SYTOX™ Blue, POPO™-1, POPO™-3, BOBO™-1, BOBO™-3, LO-PRO™-1, JO-PRO™-1, YO-PRO™ 1, TO-PRO™ 1, SYTO™ 11, SYTO™ 13, SYTO™ 15, SYTO™ 16, SYTO™ 20, SYTO™ 23, TOTO™-3, YOYO™ 3, GelStar™ and thiazole orange.

The intercalating dyes intercalate specifically into double-stranded nucleic acid molecules to generate signals. Before the extended duplex is formed, the fluorescent intensity becomes decreased; whereas by the formation of the extended duplex, the fluorescent intensity from the single fluorescent label becomes increased. Therefore, it is possible to detect a signal change that increases upon formation of the extended duplex in real time. Alternatively, it is possible to detect a signal change that decreases by the melting of the extended duplex.

(v) At Least One Label Linked to a Detection Oligonucleotide

The present invention may employ at least one label linked to a detection oligonucleotide for providing the signal indicative of the presence of the extended duplex.

The term used herein "detection oligonucleotide" is an oligonucleotide which is involved in generation of signal to be detected. According to an embodiment of the present invention, the detection oligonucleotide includes an oligonucleotide which is involved in an actual signal generation. The term is intended to exclude the first dimer-forming primer, the second dimer-forming primer and its extension strand.

In this labeling system, the signal may be provided by at least one label linked to a detection oligonucleotide upon the formation of a duplex comprising the detection oligonucleotide or the cleavage of the detection oligonucleotide. The labeling system is described in detail.

(v-1) Signal Provision Upon Formation of a Duplex Comprising the Detection Oligonucleotide The signal is provided by at least one label linked to a detection oligonucleotide upon the formation of a duplex comprising the detection oligonucleotide.

The term "a duplex comprising the detection oligonucleotide" as used herein refers to a duplex in which either strand of the duplex is the detection oligonucleotide. The term is intended to encompass (i) a duplex between the detection oligonucleotide and the extended strand of first dimer-forming primer or the second dimer-forming primer, and (ii) a duplex formed in a dependent manner on cleavage of a mediation oligonucleotide specifically hybridized with extended strand of first dimer-forming primer or the second dimer-forming primer, but is not intended to encompass a dimer between the first primer and the second primer or an extended duplex thereof as described herein.

The extended strand of the first dimer-forming primer comprises (i) a first primer sequence portion and an extended sequence portion. The extended sequence in the extended strand of first dimer-forming primer may have a sequence complementary to the 5'-templating portion of the second dimer-forming primer.

The extended strand of the second dimer-forming primer comprises (i) a second primer sequence portion and an extended sequence portion. The extended sequence in the extended strand of second dimer-forming primer may have a sequence complementary to the 5'-templating portion of the first dimer-forming primer.

In a particular embodiment, the signal is generated by at least one label linked to a detection oligonucleotide upon the formation of a duplex between the detection oligonucleotide and the extended strand of first dimer-forming primer or the second dimer-forming primer.

In a particular embodiment, the signal is generated by at least one label linked to a detection oligonucleotide upon the formation of a duplex between the detection oligonucleotide and a sequence complementary to the first primer and/or the second primer, particularly a sequence complementary to the 5'-templating portion of the first primer and/or the 5'-templating portion of the second primer.

In a particular embodiment, the signal is generated by at least one label linked to an detection oligonucleotide upon the formation of a duplex between the detection oligonucleotide and the first primer and/or the second primer, particularly, the 5'-templating portion of the first primer and/or the 5'-templating portion of the second primer.

The signal by the formation of a duplex between the detection oligonucleotide and a sequence complementary to the first primer and/or the second primer or between the detection oligonucleotide and the first primer and/or the second primer may be generated by various methods, including Lux method (U.S. Pat. No. 7,537,886), Molecular Beacon method (Tyagi et al, Nature Biotechnology v. 14 MARCH 1996), HyBeacon method (French D J et al., Mol. Cell Probes, 15(6):363-374(2001)), adjacent hybridization probe method (Bernard, P. S. et al., Anal. Biochem., 273: 221(1999)) and LNA method (U.S. Pat. No. 6,977,295).

In a particular embodiment, the signal is generated by at least one label linked to a detection oligonucleotide upon the formation of a duplex in a dependent manner on cleavage of a mediation oligonucleotide specifically hybridized with the extended strand of the first primer and/or the second primer or with sequences complementary to the first primer and/or the second primer.

The term used herein "mediation oligonucleotide" is an oligonucleotide which mediates production of a duplex not containing the first primer and the second primer.

According to an embodiment of the present invention, the cleavage of the mediation oligonucleotide per se does not generate signal and a fragment formed by the cleavage is involved in successive reactions for signal generation.

According to an embodiment, the hybridization or cleavage of the mediation oligonucleotide per se does not generate signal.

According to an embodiment of the present invention, the mediation oligonucleotide includes an oligonucleotide which is hybridized with the first primer or the second primer (particularly, the 5'-templating portion of the first primer or the 5'-templating portion of the second primer).

According to an embodiment of the present invention, the mediation oligonucleotide includes an oligonucleotide which is hybridized with the extended sequence in the extended strand of the first primer or the second primer (particularly, the sequence complementary to the 5'-templating portion of the first primer or the 5'-templating portion of the second primer).

According to an embodiment of the present invention, the mediation oligonucleotide is cleaved to release a fragment, leading to mediate the production of a duplex. Particularly, the fragment mediates a production of a duplex by an extension of the fragment on a capture oligonucleotide.

According to an embodiment of the present invention, the mediation oligonucleotide comprises (i) a 3'-targeting portion comprising a hybridizing nucleotide sequence complementary to the extended strand of the first primer and/or the second primer and (ii) a 5'-tagging portion comprising a nucleotide sequence non-complementary to the extended strand of the first primer and/or the second primer.

According to an embodiment of the present invention, the mediation oligonucleotide comprises (i) a 3'-targeting portion comprising a hybridizing nucleotide sequence complementary to the first primer and/or the second primer (particularly, sequence complementary to the 5'-templating portion of the first primer or the 5'-templating portion of the second primer) and (ii) a 5'-tagging portion comprising a nucleotide sequence non-complementary to the extended strand of the first primer and/or the second primer.

According to an embodiment of the present invention, the mediation oligonucleotide comprises (i) a 3'-targeting portion comprising a hybridizing nucleotide sequence complementary to the extended sequence in the extended strand of the first primer or the second primer and (ii) a 5'-tagging portion comprising a nucleotide sequence non-complementary to the extended strand of the first primer and/or the second primer.

According to an embodiment of the present invention, the cleavage of a mediation oligonucleotide release a fragment and the fragment is specifically hybridized with a capture oligonucleotide and extended on the capture oligonucleotide.

According to an embodiment of the present invention, a mediation oligonucleotide hybridized with the first primer and/or the second primer is cleaved to release a fragment and the fragment is specifically hybridized with a capture oligonucleotide and the fragment is extended to form an extended strand, resulting in formation of another extended duplex between the extended stand and the capture oligonucleotide providing a signal indicating the presence of the extended duplex.

According to an embodiment of the present invention, where a third oligonucleotide comprising a hybridizing nucleotide sequence complementary to the extended strand is used, the hybridization of the third oligonucleotide and the extended strand forms other type of a duplex providing a signal indicating the presence of the extended duplex.

According to an embodiment of the present invention, where a third oligonucleotide comprising a hybridizing nucleotide sequence complementary to the capture oligonucleotide is used, the formation of a duplex between the third oligonucleotide and the capture oligonucleotide is inhibited by the formation of the duplex between the extended strand and the capturing oligonucleotide, leading to provide a signal indicating the presence of the extended duplex.

According to an embodiment of the present invention, the fragment, the extended strand, the capture oligonucleotide, the third oligonucleotide or combination of them can work as the detection oligonucleotide.

In the present method, to provide a signal by the duplex formed in a dependent manner on cleavage of the mediation oligonucleotide, various known methods can be referenced, including PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312).

With referring to terms disclosed in the above references, the corresponding examples of the oligonucleotides are as follows: a mediation oligonucleotide is corresponding to a PTO (Probing and Tagging Oligonucleotide), a capture oligonucleotide to a CTO (Capturing and Templating Oligonucleotide), and a third oligonucleotide to SO (Signaling Oligonucleotide) or HO (Hybridization Oligonucleotide), respectively. SO, HO, CTO, extended strand or their combination can take a role as a detection oligonucleotide.

The signal by the duplex formed in a dependent manner on cleavage of the mediation oligonucleotide includes the signal provided by inhibition of the formation of other duplex by the duplex formed in a dependent manner on cleavage of the mediation oligonucleotide (see PCE-NH).

According to an embodiment, the detection oligonucleotide includes the oligonucleotide being specifically hybridizable with the fragment-extended strand (see PCE-SH method) and oligonucleotide being specifically hybridizable with the CTO (see PCE-NH method). According to an embodiment, the detection oligonucleotide includes the fragment-extended strand produced during a reaction or CTO.

The term "PTOCE-based method" is used herein to intend to encompass various methods for providing signals comprising the formation of an extended strand through cleavage and extension of PTO.

According to an embodiment, the signal generated by the formation of a duplex includes signals induced by hybridization of the duplex (e.g., hybridization of the duplex per se, or hybridization of a third oligonucleotide) or by inhibition of hybridization of a third oligonucleotide due to the formation of a duplex.

In a particular embodiment, the signal is generated by at least one label linked to a detection oligonucleotide upon the formation of a duplex in a dependent manner on cleavage of the extended duplex of the first and second primer.

According to an embodiment of the present invention, the first and/or second primer contains an endonucleolytic site or a restriction recognition site.

According to an embodiment of the present invention, the extended duplex of the first and second primer contains an endonucleolytic site or a restriction recognition site. The endonucleolytic site or the restriction recognition site may be generated by the extension of the first primer and/or the second primer of the present invention. The endonucleolytic site or the restriction recognition site may be cleaved by the action of an endonuclease or a restriction enzyme specific for the site, to release a fragment. Particularly, the fragment mediates a production of a duplex by an extension of the fragment on a capture oligonucleotide.

According to an embodiment of the present invention, the cleavage of the extended duplex releases a fragment and the fragment is specifically hybridized with a capture oligonucleotide and extended on the capture oligonucleotide.

According to an embodiment of the present invention, the extended duplex is cleaved to release a fragment and the fragment is specifically hybridized with a capture oligonucleotide and the fragment is extended to form an extended strand, resulting in formation of another extended duplex between the extended stand and the capture oligonucleotide providing a signal indicating the presence of the extended duplex.

According to an embodiment of the present invention, where a third oligonucleotide comprising a hybridizing nucleotide sequence complementary to the extended strand is used, the hybridization of the third oligonucleotide and the extended strand forms other type of a duplex providing a signal indicating the presence of the extended duplex.

According to an embodiment of the present invention, where a third oligonucleotide comprising a hybridizing nucleotide sequence complementary to the capture oligonucleotide is used, the formation of a duplex between the third oligonucleotide and the capture oligonucleotide is inhibited by the formation of the duplex between the extended strand and the capturing oligonucleotide, leading to provide a signal indicating the presence of the extended duplex.

According to an embodiment of the present invention, the fragment, the extended strand, the capture oligonucleotide, the third oligonucleotide or combination of them can work as the detection oligonucleotide.

In the present method, to provide a signal by the duplex formed in a dependent manner on cleavage of the extended duplex, various known methods can be referenced (see Korean Patent Application 10-2017-0121700).

The signal by the duplex formed in a dependent manner on cleavage of the extended duplex includes the signal provided by inhibition of the formation of other duplex by the duplex formed in a dependent manner on cleavage of the extended duplex (see PCE-NH).

According to an embodiment, the detection oligonucleotide includes the oligonucleotide being specifically hybridizable with the extended strand (see PCE-SH method) and oligonucleotide being specifically hybridizable with the CTO (see PCE-NH method). According to an embodiment, the detection oligonucleotide includes the extended strand produced during a reaction or CTO.

(v-2) Signal Provision by Cleavage of the Detection Oligonucleotide

The signal is provided by at least one label linked to a detection oligonucleotide upon the cleavage of the detection oligonucleotide.

In a particular embodiment, the signal is generated by at least one label linked to a detection oligonucleotide upon the hybridization of the detection oligonucleotide with the extended strand of the first dimer-forming primer or the second dimer-forming primer and then cleavage of the detection oligonucleotide.

In a particular embodiment, the signal is generated by at least one label linked to a detection oligonucleotide upon the hybridization of the detection oligonucleotide with the first primer and/or the second primer, particularly with the 5'-templating portion of the first primer and/or the 5'-templating portion of the second primer, and then cleavage of the detection oligonucleotide.

In a particular embodiment, the signal is generated by at least one label linked to a detection oligonucleotide upon the hybridization of the detection oligonucleotide with a sequence complementary to the first primer or the second primer, particularly with a sequence complementary to the 5'-templating portion of the first primer or the 5'-templating portion of the second primer, and then cleavage of the detection oligonucleotide.

The signal by hybridization of the detection oligonucleotide with the first primer and/or the second primer or with a sequence complementary to the 5'-templating portion of the first primer and/or the 5'-templating portion of the second primer and then cleavage of the detection oligonucleotide may be generated by various methods, including TaqMan probe method (U.S. Pat. Nos. 5,210,015 and 5,538,848).

Where the signal is generated by TaqMan probe method, a detection oligonucleotide having a suitable label (e.g., interactive dual label) and a nucleic acid polymerase having 5'-nuclease activity are used. The detection oligonucleotide hybridized with the first primer and/or the second primer is cleaved during extension of the first primer and/or the second primer and generates signal indicative of the presence of an extended duplex.

In a particular embodiment, the signal is generated by at least one label linked to a detection oligonucleotide upon the cleavage of the detection oligonucleotide in a dependent manner on cleavage of a mediation oligonucleotide specifically hybridized with the extended strand of the first dimer-forming primer or the second dimer-forming primer.

In a particular embodiment, the signal is generated by at least one label linked to a detection oligonucleotide upon the cleavage of the detection oligonucleotide in a dependent manner on cleavage of a mediation oligonucleotide specifically hybridized with the first primer and/or the second primer, particularly with the 5'-templating portion of the first primer and/or the 5'-templating portion of the second primer.

In a particular embodiment, the signal is generated by at least one label linked to a detection oligonucleotide upon the cleavage of the detection oligonucleotide in a dependent manner on cleavage of a mediation oligonucleotide specifically hybridized with a sequence complementary to the first primer and/or the second primer, particularly with a sequence complementary to the 5'-templating portion of the first primer and/or the 5'-templating portion of the second primer.

According to an embodiment of the present invention, where a mediation oligonucleotide hybridized with the first primer and/or the second primer is cleaved to release a fragment, and the fragment is specifically hybridized with a detection oligonucleotide and the fragment induces the cleavage of the detection oligonucleotide.

According to an embodiment of the present invention, where a mediation oligonucleotide hybridized with the first primer and/or the second primer is cleaved to release a fragment, the fragment is extended to cleave a detection oligonucleotide comprising a hybridizing nucleotide sequence complementary to the capture oligonucleotide.

In the present method, to provide a signal by cleavage of the detection oligonucleotide in a dependent manner on cleavage of the mediation oligonucleotide, various known methods can be referenced, including Invader assay (U.S. Pat. Nos. 5,691,142, 6,358,691 and 6,194,149), PCEC (PTO Cleavage and Extension-Dependent Cleavage) method (WO 2012/134195) and a method described in U.S. Pat. No. 7,309,573. In particular, the method described in U.S. Pat. No. 7,309,573 may be considered as one of PTOCE-based methods using signal generation by cleavage, and in the method, the formation of the extended strand may be detected by detecting cleavage of an oligonucleotide specifically hybridized with the CTO by the formation of the extended strand. Invader assay forms a fragment by cleavage of a mediation oligonucleotide and induces successive cleavage reactions with no extension of the fragment.

According to an embodiment of the present invention, where the signal is generated in a dependent manner on cleavage of a detection oligonucleotide, the cleavage of the detection oligonucleotide induces signal changes or releases a labeled fragment to be detected.

Where the signal is generated by cleavage of the detection oligonucleotide, a released label by the cleavage may be detected at any temperatures.

According to an embodiment, the detection oligonucleotide comprises at least one label. According to an embodiment of the present invention, the detection oligonucleotide may be composed of at least one oligonucleotide. According to an embodiment of the present invention, where the detection oligonucleotide is composed of a plurality of oligonucleotides, it may have a label in various manners. For instance, one oligonucleotide among a plurality of oligonucleotides may have at least one label, a plurality of oligonucleotides all may have at least one label, or one portion of oligonucleotides may have at least one label and the other portion may not have a label.

In a particular embodiment, the signal is generated by cleavage of the detection oligonucleotide in a dependent manner on cleavage of the extended duplex of the first and second primer.

According to an embodiment of the present invention, the first and/or second primer contains an endonucleolytic site or a restriction recognition site.

According to an embodiment of the present invention, the extended duplex contains an endonucleolytic site or a restriction recognition site. The endonucleolytic site or the restriction recognition site may be generated by the extension of the first primer and/or the second primer of the present invention. The endonucleolytic site or the restriction recognition site may be cleaved by the action of an endonuclease or a restriction enzyme specific for the site.

According to an embodiment of the present invention, the extended duplex is cleaved to release a fragment.

Methods using cleavage of the detection oligonucleotide in a dependent manner on cleavage of a mediation oligonucleotide can be applicable for signal generation.

Step (c): Detection of Signal 130

Next, the detectable signal is detected during or after the amplification reaction. The detection of the signal indicates the presence of the extended duplex, and the presence of the extended duplex indicates amplification (extension) of the extended duplex.

As described above, the formation of the extended duplex, the formation of a duplex containing the detection oligonucleotide, or the cleavage of the detection oligonucleotide provides a signal indicative of the presence of the extended duplex through signaling from the labels. Thus, the label of the extended duplex, or the detection oligonucleotide can provide a detectable signal in real time upon formation of the extended duplex or a duplex containing the detection oligonucleotide, or it can provide a detectable signal upon melting of the extended duplex or a duplex containing the detection oligonucleotide or upon hybridization after the melting.

In an embodiment of the present invention, the detection of the signal is performed in a real-time manner, an end-point manner, or a predetermined time interval manner. The real-time detection of the signal herein comprises detecting the signal provided by the formation of the extended duplex, the formation of a duplex containing the detection oligonucleotide, or the cleavage of the detection oligonucleotide at each repeating cycle.

In an embodiment of the present invention, the detection of the signal is performed at one or more temperatures.

In a particular embodiment of the present invention, the detection of the signal is performed at one or more temperatures during or after the amplification reaction.

In a particular embodiment of the present invention, the detection of the signal is performed at one, two or three temperatures during the amplification reaction.

In a particular embodiment of the present invention, the detection of the signal is performed over a temperature range while gradually increasing or decreasing the temperature during the amplification reaction.

In a particular embodiment of the present invention, the detection of the signal is performed over a temperature range while gradually increasing or decreasing the temperature after the amplification reaction.

The detection of the signal over a temperature range while gradually increasing or decreasing the temperature during or after the amplification reaction can be referred to herein as the melting analysis.

According to another embodiment, the detection of the signal is carried out by a melting analysis.

The term "melting analysis" as used herein means a method in which a signal indicative of the presence of the extended duplex is obtained by melting of the extended duplex or melting of a duplex containing the detection oligonucleotide, including a method to measure signals at two different temperatures, melting curve analysis, melting pattern analysis and melting peak analysis. Particularly, the melting analysis is a melting curve analysis.

For example, when the extended duplex or is melted, the reporter molecule and the quencher molecule on the single-stranded first primer are conformationally adjacent to each other to allow the quencher molecule to quench the signal from the reporter molecule. In contrast, when the two primers hybridize again with each other to form an extended duplex, the reporter molecule and the quencher molecule are conformationally separated to allow the quencher molecule to unquench the signal from the reporter molecule, giving rise to changes in signals.

In an embodiment, the amplification reaction further comprises denaturing the extended duplex, hybridizing denatured strands with the first primer and the second primer, and extending the first primer and the second primer to form the extended duplex.

Without wishing to be bound by any theory, an extended duplex may be formed by two fashions: (a) an extended duplex, which is formed by hybridization between and the extension of the two primers; and (b) an extended duplex, which is formed by hybridization between the first primer and an extension product of the second primer (or hybridization between the second primer and an extension product of the first primer) and the extension of the first primer. Since the structures of the two extended duplexes are the same, the two extended duplexes should be construed as being encompassed by the extended duplex of the present invention.

The method further comprises melting the extended duplex or melting the extended duplex followed by hybridization between the steps (b) and (c) to provide a detectable signal, and the step (c) is performed by detecting the signal provided by the melting or the melting followed by hybridization.

The melting curve or hybridization curve may be obtained by conventional technologies, for example, as described in U.S. Pat. Nos. 6,174,670 and 5,789,167, Drobyshev et al, *Gene* 188: 45(1997); Kochinsky and Mirzabekov *Human Mutation* 19:343(2002); Livehits et al *J. Biomol. Structure Dynam.* 11:783(1994); and Howell et al *Nature Biotechnology* 17:87(1999). For example, a melting curve or hybridization curve may consist of a graphic plot or display of the variation of the output signal with the parameter of hybridization stringency. Output signal may be plotted directly against the hybridization parameter. Typically, a melting curve or hybridization curve will have the output signal, for example fluorescence, which indicates the degree of duplex structure (i.e. the extent of hybridization), plotted on the Y-axis and the hybridization parameter on the X axis.

According to one embodiment of the present invention, the method further comprises repeating the steps (b)-(c) with denaturation between repeating cycles. This repetition permits to amplify the pair of dimer-forming primers and/or the signal.

Step (d): Obtaining an Indicator Indicative of Amplification 140

Next, an indicator indicative of amplification is obtained from the signal detected in step (c).

The term "indicator indicative of amplification" refers to any indicator which is closely related to the occurrence of amplification (or extension) of a pair of dimer-forming primers, obtainable from the signal detected in step (c). The indicator is meant by a value generated in a dependent manner on the amplification of the pair of dimer-forming primers. The indicator may provide a larger value or a smaller value as the amplification of the pair of dimer-forming primers increases. The indicator can be any indicator as long as it indicates amplification.

The indicator may be used directly in the performance evaluation of step (e). Alternatively, the indicator may be used indirectly after further modification and processing thereof. The indicator may be a numerical value, a form, or any other expression.

The indicator may include one obtained from an amplification curve or a melting curve. In particular, the indicator may include a signal value (e.g., RFU) at a particular cycle, a signal value at each cycle, or a difference in signal values at particular cycles in an amplification curve, or height, width or area of the maximum melting peak in a melting curve.

In one embodiment, the indicator is selected from the group consisting of Ct (cycle threshold), ΔRFU (e.g., difference in RFUs at two cycles), RFU ratio (e.g., ratio of RFUs at two cycles), End-RFU (RFU at the end point), a melting peak height (e.g., height of the maximum peak in a melting curve), a melting peak width (e.g., width of the maximum peak in a melting curve), a melting peak area (e.g., area under the maximum peak in a melting curve), and a combination thereof.

According to one embodiment of the present invention, the indicator indicative of amplification is the Ct value. The Ct value may be a crossing point between an amplification curve and a threshold line. The Ct value may be a first derivative maximum or a second derivative maximum. The Ct value is well known in the art.

According to one embodiment of the present invention, the indicator indicative of amplification is the ΔRFU or RFU ratio in an amplification curve. For example, the indicator is the difference (subtraction) or ratio (division) between RFUs at two cycles. For example, the indicator is the difference or ratio between a RFU value at a start cycle or at background region and a RFU values at an end cycle or at plateau region in an amplification curve. The RFU ratio includes the signal-to-noise ratio in the real-time PCR results.

According to one embodiment of the present invention, the indicator indicative of amplification is the End-RFU. The End-RFU indicates a RFU value at an end point of the amplification reaction, i.e., a RFU value at an end cycle of an amplification curve. The concept of End-RFU value is well known in the art.

According to one embodiment of the present invention, the indicator indicative of amplification is the melting peak height. The melting peak height refers to the height of the maximum peak in the derivative of the mating curve obtained for the melting analysis. The melting analysis includes detecting a signal generated by the melting of the duplex formed after the completion of the amplification reaction or detecting a signal generated by hybridization after melting the formed duplex. The term "melting assay" as used herein is used to encompass the melting assay in a narrow sense as well as the hybridization assay unless otherwise specified. The melting analysis in a narrow sense means a method of measuring dissociation of a duplex under increasing stringent conditions by controlling temperatures. The hybridization assay in a narrow sense means a method of measuring association of a duplex under decreasing stringent conditions by controlling temperatures.

According to one embodiment of the present invention, the indicator indicative of amplification is the melting peak width or area. The melting peak width or area indicates the width or area of the maximum peak in the derivative of the melting curve obtained for the melting analysis. The melting peak width or area is well known in the art.

The indicators as described above are closely related to the occurrence of amplification (or extension) of the pair of dimer-forming primers in the amplification reaction. A change in the performance of components in an amplification composition or an amplification device affects the amplification reaction, leading to changes in the indicator. For instance, components having relatively high performance will have reduced Ct value, increased End-RFU, or increased melting peak height, width, or area compared to components having relatively poor performance. Therefore, the performance of the components can be easily evaluated by the indicator obtained.

Step (e): Evaluation of the Performance of Component 150

Finally, the performance of the component is evaluated based on the indicator obtained in step (d).

The phrase "evaluating the performance of the component based on the indicator" as used herein means evaluating the performance of the component directly using the indicator, or indirectly using the indicator after further modification and processing.

The indicator includes Ct (cycle threshold), ΔRFU, RFU ratio, End-RFU, a melting peak height, a melting peak width, a melting peak area, and a combination thereof, and the magnitude of the indicator can be used to evaluate the performance of the component.

The term "component" refers to an element involved in the amplification reaction. In particular, the component herein refers to an element that has a significant effect on the amplification reaction, or on the result or the interpretation thereof.

In an embodiment, the component herein is any component in an amplification composition as well as any component in an amplification device. In an embodiment, the component is any sample prepared for detection of a nucleic acid sequence of interest.

Meanwhile, the term "component of interest" or "component to be evaluated" as used herein refers to a component selected to evaluate its performance. Component of interest may be selected prior to performing the method of the present invention by a user of the present invention.

The term "performance" as used herein in connection with a component of interest refers to the ability or activity of a component of interest to promote or inhibit an amplification reaction or detection reaction, or the effect of a component of interest on an amplification reaction or detection reaction. The performance may be defined differently depending on the selected component.

For example, the performance of a nucleic acid polymerase is its polymerization activity; the performance of a label is its signaling performance; the performance of dNTPs is the ability to be incorporated during formation of new extended strands; the performance of a buffer is the ability to provide an environment for amplification (extension); the performance of magnesium ion is the ability to assist the activity of the nucleic acid polymerase; the performance of the additive is the ability to contribute to the amplification reaction; the performance of an amplification device is the temperature-controlling ability and/or detection sensitivity in the amplification reaction.

In one embodiment of the present invention, the component to be evaluated is a nucleic acid polymerase, and the performance of the component is its polymerization activity.

In another embodiment of the present invention, the component to be evaluated is a label, and the performance of the component is its signaling performance.

In another embodiment of the present invention, the component to be evaluated is a thermocycler and/or a detector, and the performance of the component is its temperature-controlling ability and/or detection sensitivity in the amplification reaction.

In another embodiment of the present invention, the component to be evaluated is a reaction vessel, the performance of the component is its temperature transfer ability or light transmission ability.

In another embodiment of the present invention, the component to be evaluated is the sample, and the performance of the component is its inhibitory activity against the amplification reaction. Samples may include an inhibitory element against the performance of components, in particular, an inhibitory element to degrade primers or probes to be used. Therefore, the amplification composition further comprises a sample prepared for detection of a nucleic acid sequence of interest, and the sample is examined whether there is such an inhibitory element in the sample.

The performance of the component can be evaluated in various ways. Since the technical feature of the present invention is to evaluate the performance of the component using a pair of dimer-forming primers as described above. Therefore, the present invention is not particularly limited to the use of a specific indicator. Although some examples of indicators are described below, it should be understood that various modifications can be made by those skilled in the art.

Specifically, the performance of the component can be determined by the indicator per se obtained in step (d), or by comparing the indicator obtained in step (d) with a reference indicator.

In one embodiment, the performance of the component can be determined by the indicator per se obtained in step (d).

The evaluation can be accomplished by obtaining an indicator from an amplification reaction under standard conditions except for the amplification-related factor to be evaluated and regarding the obtained indicator as the performance of the component. For example, for evaluating the performance of a nucleic acid polymerase, an amplification reaction is performed under predetermined conditions using the nucleic acid polymerase. The predetermined conditions refer to conditions in which the types and amounts of components and the type of an amplification device as well as temperature, etc. for an amplification reaction are the same. Thereafter, an indicator is obtained from the amplification reaction, and the indicator is regarded as the performance of the nucleic acid polymerase. The indicator indicates the performance of the nucleic acid polymerase under predetermined conditions. Likewise, other nucleic acid polymerases can also be evaluated based on the indicator obtained by another amplification reaction under the predetermined conditions.

In one embodiment, the performance of the component can be determined by comparing the indicator obtained in step (d) with a reference indicator obtained from a reference reaction.

The term "reference reaction" as used herein refers to any reaction that is compared to an amplification reaction using a component to be evaluated. The reference reaction refers to a separate reaction using a reference component instead of a component to be evaluated.

The term "reference component" as used herein refers to an element used for comparison with a component of interest. The reference component refers to a component that differs in any different characteristic, such as the type, quantity, or manufacturing time, from a component to be evaluated by the present method. For example, when the performance of bacteriophage DNA polymerase is to be evaluated, the reference component may be Taq polymerase; when the performance of a specific quantity of Taq polymerase is to be evaluated, the reference component may be a different quantity of Taq polymerase.

The reference reaction can be carried out by the method of the present invention using a reference component instead of the component of interest. The reference component may be one corresponding to the component of interest. The reference component may be a component having a known performance, or a control component selected by the user for comparison but not having known performance.

A "reference indicator" is obtained by an amplification reaction using the reference component. The term "reference indicator" as used herein refers to an indicator obtained from an amplification reaction using a reference component in order to compare it with an, indicator for a component of interest.

Specifically, the reference reaction can be performed by carrying out the method of the present invention using a reference component instead of the component of interest, and a reference indicator can be obtained from the reference reaction.

The reference indicator may be obtained from a single reaction using a single reference component, or may be obtained from a plurality of reference reactions using a single reference component. When the reference indicator is obtained from a plurality of reference reactions, the reference indicator may be an average of reference indicators obtained from a plurality of reference reactions, or a range of reference indicators obtained from a plurality of reference reactions, or any value within the range.

As an example, after conducting the method of the present invention using a reference nucleic acid polymerase having a known activity, the obtained Ct value may be used as a "reference indicator". As another example, after repetitively conducting the method of the present invention using a reference nucleic acid polymerase having a known activity, an average of the obtained Ct values, a range of the obtained Ct values, or any value within the range may be used as a reference indicator.

The reference indicator is compared with the indicator obtained for the component of interest. The comparison may include determining the magnitude of the two indicators or calculating another value from the two indicators. A comparison with the reference indicator can allow for determining whether the performance of the component of interest is good or poor compared with the reference indicator.

The determination of the performance of the component of interest may depend on the indicator used. For example, when the indicator used is the Ct value, a large indicator may indicate poor performance; whereas when the indicator used is the End-RFU or melting peak height, a large indicator may indicate good performance.

In one embodiment using the reference indicator, the performance of the component can be determined by comparison with a standard curve.

The standard curve can be prepared by obtaining a plurality of reference indicators by amplification reactions using a plurality of reference components having known performance and then plotting the plurality of reference indicators against the performance. Thereafter, an indicator can be obtained using a component of interest, and the indicator can be compared with the standard curve to determine the performance of the component.

As an example, the performance of a nucleic acid polymerase of interest can be evaluated using a standard curve as follows.

First, amplification reactions are performed using various units of nucleic acid polymerases to obtain two or more Ct values. Subsequently, the obtained Ct values are plotted against a unit of nucleic acid polymerase to obtain a standard curve.

Next, another amplification reaction is carried out using a nucleic acid polymerase of interest to obtain a Ct value. Subsequently, the obtained Ct value is compared with a standard curve to calculate the unit of the corresponding nucleic acid polymerase. Based on the results, the unit of nucleic acid polymerase of interest can be calculated.

Specifically, the performance of various components can be evaluated as follows.

(1-1) Performance Evaluation of Nucleic Acid Polymerase

The performance of a nucleic acid polymerase of interest can be determined by the indicator per se obtained under predetermined conditions or by comparison of the indicator obtained under predetermined conditions with a reference indicator.

The performance evaluation by the indicator per se can be accomplished by subjecting the nucleic acid polymerase of interest to an amplification reaction under predetermined conditions and then regarding the obtained indicator (for example, Ct value, $\Delta$RFU, RFU ratio, End-RFU, a melting peak, a melting peak width, a melting peak area, and a combination thereof) as the performance of the nucleic acid polymerase.

The performance evaluation by comparison of the indicator obtained under predetermined conditions with a reference indicator can be accomplished as follows.

First, a reference nucleic acid polymerase having a known polymerization activity (or unit) is selected. Amplification reactions using the reference nucleic acid polymerase are performed repeatedly to obtain a plurality of indicators. An average of the obtained indicators is taken as a "reference indicator".

Next, another amplification reaction using a nucleic acid polymerase of interest is performed to obtain an indicator. The obtained indicator is compared with the reference indicator.

As a result of the comparison, when the indicator for the nucleic acid polymerase of interest indicates good amplification as compared with the reference indicator for the reference nucleic acid polymerase, the performance of the nucleic acid polymerase of interest is determined to be superior to that of the reference nucleic acid polymerase; whereas when the indicator for the nucleic acid polymerase of interest indicates poor amplification as compared with the reference indicator for the reference nucleic acid polymerase, the performance of the nucleic acid polymerase of interest is determined to be inferior to that of the reference nucleic acid polymerase.

For example, assuming that the Ct value obtained by the amplification reaction using the reference nucleic acid polymerase is "30", a nucleic acid polymerase having the Ct value "20" can be determined to have superior performance to the reference nucleic acid polymerase. As another example, assuming that the Ct value obtained by the amplification reaction using the reference nucleic acid polymerase is "30", a nucleic acid polymerase having the Ct value "40" can be determined to have inferior performance to the reference nucleic acid polymerase.

The superior or good performance of a nucleic acid polymerase means that the nucleic acid polymerase has a higher polymerization activity than the reference nucleic acid polymerase.

Typically, the evaluation of the performance of components has been performed by real-time PCR methods using a template DNA from a standard strain and primers and a labeled probe for amplifying the template DNA. However, these methods have serious drawbacks in accurately determining the performance of actual components, as follows: (i) difficulty in optimizing reaction conditions and sequences of primers and a probe used; (ii) possibility of non-specific interference between components used; (iii) low sensitivity of the reaction.

In contrast, the method of the present invention can overcome the drawbacks by using a pair of dimer-forming primers, in place of the template, primer(s) and probe(s).

(1-2) Performance Evaluation of Thermocycler and/or Detector

The performance of a thermocycler and/or a detector can be determined by an indicator per se obtained under predetermined conditions or by comparison of the indicator obtained under predetermined conditions with a reference indicator.

The performance evaluation by the indicator per se can be accomplished by subjecting an amplification composition having a predetermined composition and concentration to a thermocycler and/or a detector under the predetermined conditions in an amplification device of interest and then regarding the obtained indicator as the performance of the thermocycler and/or the detector.

The performance evaluation by comparison of the indicator obtained under predetermined conditions with a reference indicator can be accomplished as follows.

First, a reference thermocycler and/or detector having a known temperature-controlling ability and/or detection sensitivity are selected. Amplification reactions using the reference thermocycler and/or detector are performed repeatedly to obtain a plurality of indicators. An average of the obtained indicators is taken as a "reference indicator".

Next, another amplification using the reference thermocycler and/or detector of interest is performed to obtain an indicator. The obtained indicator is compared with the reference indicator.

As a result of the comparison, when the indicator for the amplification device of interest indicates good amplification as compared with the reference indicator for the reference amplification device, the performance of the thermocycler and/or detector of interest is determined to be superior to that of the reference amplification device; whereas when the indicator for the thermocycler and/or detector of interest indicates poor amplification as compared with the reference indicator for the reference amplification device, the performance of the amplification device of interest is determined to be inferior to that of the reference amplification device.

For example, assuming that the End-RFU value obtained by the amplification reaction using the reference thermocycler and/or detector is "5000", a thermocycler and/or a detector having the End-RFU value "4000" can be determined to have inferior performance to the reference thermocycler and/or detector. As another example, assuming that the End-RFU value obtained by the amplification reaction using the reference thermocycler and/or detector is "5000", a thermocycler and/or a detector having the End-RFU value "6000" can be determined to have superior performance to the reference thermocycler and/or detector.

The good performance of the amplification device means that the amplification device has a higher temperature-controlling ability and/or detection sensitivity in the amplification reaction.

(1-3) Performance Evaluation of Label

The performance of a label may be determined by the indicator per se obtained under predetermined conditions or by comparison of the indicator obtained under predetermined conditions with a reference indicator.

The performance evaluation by the indicator per se can be accomplished by subjecting the label of interest to an amplification reaction under the predetermined conditions and then regarding the obtained indicator as the performance of the label.

The performance evaluation by comparison of the indicator obtained under predetermined conditions with a reference indicator can be performed as follows.

First, a pair of dimer-forming primers having a reference label corresponding to the label of interest is selected. The corresponding reference label may be a label having the same signaling mode as the label of interest. For example, if the label of interest is a single label, the corresponding reference label is also a single label. If the label of interest is an interactive dual label, the corresponding reference label is also an interactive dual label. The corresponding reference label may be a label having the different signaling mode as the label of interest.

The reference label may have of a different type or a different combination of labels, or may be linked to a different site on an oligonucleotide, compared with the label of interest.

Amplification reactions using the reference label are performed repeatedly to obtain a plurality of indicators. An average of the obtained indicators is taken as a "reference indicator".

Next, another amplification reaction using a label of interest is performed to obtain an indicator. The obtained indicator is compared with the reference indicator.

As a result of the comparison, when the indicator for the label of interest indicates good amplification as compared with the reference indicator for the reference label, the performance of the label of interest is determined to be superior to that of the reference label; whereas when the indicator for the label of interest indicates poor amplification as compared with the reference label, the performance of the label of interest is determined to be inferior to that of the reference label.

For example, assuming that the End-RFU value obtained by the amplification reaction using the reference label is "5000", a label having the End-RFU value "4000" can be determined to have inferior performance to the reference label. As another example, assuming that the End-RFU value obtained by the amplification reaction using the reference label is "5000", a label having the End-RFU value "6000" can be determined to have superior performance to the reference label.

The good performance of a label means that the label has a higher signaling performance than the reference label.

The above-described methods for evaluating the performance of components can be used in combination with various conventional methods. Conventional methods to be used in combination are found in Richardson, C. D. et al. (1964) J. Biol. Chem. 239, 222-232; Griep, M. A. (1995) Anal. Biochem. 232, 180-189; Seville, M., et al. (1996) Biotechniques 21, 664, 668, 670, 672; Tveit, J. et al. (2001) Anal. Biochem. 289, 96-98; Yu, Liming, et al. (2002) Biotechniques 33, 938-941; Ma, C. et al. (2006) Anal. Biochem. 353, 141-143); Luo, X. et al. (2011) Electroanalysis 23 923-926.

II. Application of the Method of the Present Invention

The method for evaluating the performance of components according to the present invention can be applied in various ways.

(i) Quality Control

The method of the present invention can also be applied to quality control (QC) of components. The quality of components may vary from batch to batch or over time. Thus, the quality of components can be controlled by evaluating the performance of the components in each batch using the method of the present invention, or by evaluating the performance of the components in a batch over time.

For example, the performance of two nucleic acid polymerases produced in a reference batch and a new batch is evaluated by the method of the present invention. Then, the performance of the nucleic acid polymerase in the new batch is compared with that of the nucleic acid polymerase in the reference batch to determine whether the nucleic acid polymerase in the new batch is suitable for use.

Alternatively, the activity of a nucleic acid polymerase can be compared before and after the lapse of a predetermined time to determine whether the activity of the nucleic acid polymerase decreases over time.

(ii) Shelf Life Setting

The method of the present invention can be applied for setting the shelf life of components. For example, the activity of the nucleic acid polymerase is evaluated at a predetermined time interval from the initial production. If the activity falls below a predetermined level after a certain period of time, the time can be determined as the shelf life of the nucleic acid polymerase.

(iii) Internal Control

A pair of dimer-forming primers according to the method of the present invention can be used as an internal control.

In general, an internal control is used to monitor the inhibitory activity of the sample against an amplification reaction or the nucleic acid extraction process. The internal control includes: (i) a template irrelevant to a target nucleic acid sequence suspected of being contained in a sample and (ii) primers and probes for amplifying and detecting the template. In order to satisfy the requirement as an internal control, the amplification efficiency of the internal control should not be affected by the amplification of the target nucleic add sequence contained in the sample, and vice versa.

The amplification of an internal control indicates that the sample has no inhibitory activity against the amplification reaction, i.e., the sample contains no substances that inhibit the amplification reaction.

A pair of dimer-forming primers according to the present invention can replace the components of a conventional internal control, i.e., a template, a primer and a probe. A pair of dimer-forming primers according to the present invention can be further added to an amplification reaction of a target nucleic acid sequence in a sample, so that amplification of the pair of dimer-forming primers can occur simultaneously with amplification of the target nucleic add sequence. The amplification of the pair of dimer-forming primers can allow the determination of whether an inhibitory substance against the amplification reaction is present in a sample.

The use of a pair of dimer-forming primers according to the present invention can be embodied as follows.

First, in step (a) of the present method, a sample prepared for detection of a nucleic acid sequence of interest is further added to an amplification composition comprising a pair of dimer-forming primers.

The amplification composition may comprise components for amplifying the pair of dimer-forming primers, as well as components for amplifying the target nucleic acid sequence contained in the sample. Specifically, the amplification composition may include a pair of dimer-forming primers and a nucleic acid polymerase, dNTPs, a buffer, a salt and the like for amplifying the pair of dimer-forming primers, as well as a sample and a primer, a probe, a nucleic acid polymerase, dNTPs, a buffer, a salt, and the like for amplifying the target nucleic acid sequence. Among the components, a nucleic acid polymerase, dNTPs, buffer, salt, and the like may be commonly used for both amplification of the pair of dimer-forming primers and amplification of the target nucleic acid sequence. However, so as to distinguish between a signal generated by amplification of the pair of dimer-forming primers and a signal generated by amplification of the target nucleic acid sequence, it is preferred that the labeling system used in the pair of dimer-forming primers and the labeling system used in the probe for amplifying the target nucleic acid sequence are different from each other. For example, the label used in the pair of dimer-forming primers may emit light at a wavelength different from the label used in the probe.

Next, in the step (b), the amplification composition is subjected to an amplification reaction. During this reaction, if the sample has no inhibitory substance, the pair of dimer-forming primers will form an extended duplex, thereby providing a detectable signal. However, if the sample has an inhibitory substance, the pair of dimer-forming primers will fail to form an extended duplex, thereby providing a significantly low signal. Thus, the presence or absence of an inhibitory substance in a sample can be determined by measuring the signal from the pair of dimer-forming primers. As such, the pair of dimer-forming primers according to the present invention can be used as an internal control.

According to embodiments using the pair of dimer-forming primers of the present invention as an internal control, the component to be evaluated is a sample, and the performance of the component is an inhibitory activity against the amplification reaction.

(iv) Quantification Standard

A pair of dimer-forming primers according to the method of the present invention can be used as a quantification standard.

Conventionally, quantification of a target nucleic acid sequence is accomplished by performing amplification reactions using a dilution series of a known standard to obtain a standard curve in which a log value of the initial amount of the target nucleic acid sequence is plotted against a Ct value, and then comparing a Ct value obtained from an unknown sample with the standard curve to calculate the amount of the target nucleic acid sequence in the sample. The pair of dimer-forming primers can be used in place of the standard.

The method of the present invention can be performed using a plurality of pairs of dimer-forming primers. The plurality of pairs of dimer-forming primers can form a plurality of extended duplexes, thereby providing signals that are distinguished from each other.

For example, when two pairs of dimer-forming primers are used, e.g., a first primer pair consisting of a first primer and a second primer and a second primer pair consisting of a third primer and a fourth primer, the first primer and the second primer form a first extended duplex, the third primer and the fourth primer form a second extended dimer, and each of the first extended duplex and the second extended duplex has a labeling system capable of generating different signals.

The use of a plurality of pairs of dimer-forming primers can allow a more sensitive measurement of the polymerization activity of the nucleic acid polymerase compared with a single pair of dimer-forming primers. When a plurality of pairs of dimer-forming primers each have different preferences for amplification, i.e., different degrees of amplification, the amplification of each pair of dimer-forming primers will depended on the polymerization activity of a nucleic acid polymerase. For example, a polymerase with high polymerization activity will significantly amplify all of the plurality of pairs of dimer-forming primers, while a polymerase with low polymerization activity will amplify some of the plurality of pairs of dimer-forming primers. Therefore, the activity of the nucleic acid polymerase can be evaluated by monitoring the amplification of a plurality of pairs of dimer-forming primers. That is, when a plurality of pairs of dimer-forming primers are used, the activity of the nucleic acid polymerase can be evaluated by measuring the activity of the nucleic acid polymerase using each pair of dimer-forming primers and combining the results.

III. Kit

In another aspect of the present invention, there is provided a kit for evaluating the performance of a component in an amplification composition or an amplification device, comprising:

a pair of dimer-forming primers comprising a first primer and a second primer;

wherein the first primer and the second primer each comprise a 3'-dimer-forming portion; wherein a nucleotide sequence of the 3'-dimer-forming portion in the first primer is complementary to a nucleotide sequence of the 3'-dimer-forming portion in the second primer; wherein the first primer and the second primer form a dimer through hybridization between the 3'-dimer-forming portions under amplification conditions, and are each extended by a nucleic acid polymerase to form an extended duplex.

Since the kit of this invention is constructed to perform the detection method of the present invention described above, the common descriptions between them are omitted in order to avoid undue redundancy leading to the complexity of this specification.

According to one embodiment of the present invention, a nucleotide sequence of the 3'-dimer-forming portion in the first primer is complementary to a nucleotide sequence of the 3'-dimer-forming portion in the second primer.

According to one embodiment of the present invention, the 3'-dimer-forming portions of the first primer and the second primer each have 2 or less non-complementary nucleotide so long as the hybridization between the 3'-dimer-forming portions is not significantly affected.

According to one embodiment of the present invention, the 3'-dimer-forming portions of the first primer and the second primer have nucleotide sequences perfectly complementary to each other.

The 3'-dimer forming portions of the first primer and the second primer are 3 to 50 nucleotides in length, respectively. In an embodiment of the present invention, the 3'-dimer-forming portions of the first primer and the second primer each are 3, 4, 5, 6, 7, 8, 9, 10, 11, 12, 13, 14, 15, 16, 17, 18, 19, 20, 21, 22, 23, 24, 25, 30, 40 or 50 nucleotides in length. For example, the 3'-dimer-forming portions of the first and second primers each are 3-50, 3-40, 3-35, 3-30, 3-25, 3-20, 3-17, 3-15, 3-12, 3-10, 3-9, 3-8, 3-7, 3-6, 3-5, 3-4, 4-50, 4-40, 4-35, 4-30, 4-25, 4-20, 4-17, 4-15, 4-12, 4-10, 4-9, 4-8, 4-7, 4-6, 4-5, 5-50, 5-40, 5-35, 5-30, 5-25, 5-20, 5-17, 5-15, 5-12, 5-10, 5-9, 5-8, 5-7, 5-6, 6-50, 6-40, 6-35, 6-30, 6-25, 6-20, 6-17, 6-15, 6-14, 6-13, 6-12, 6-11, 6-10, 6-9, 6-8, 6-7, 7-50, 7-40, 7-35, 7-30, 7-25, 7-20, 7-19, 7-18, 7-17, 7-16, 7-15, 7-14, 7-13, 7-12, 7-11, 7-10, 7-9, 7-8, 8-50, 8-40, 8-35, 8-30, 8-25, 8-20, 8-17, 8-15, 8-12, 8-10, 8-9, 9-50, 9-40, 9-35, 9-30, 9-25, 9-20, 9-17, 9-15, 9-12, 9-10, 10-50, 10-40, 10-35, 10-30, 10-25, 10-20, 10-17, 10-15, 10-12, 12-50, 12-40, 12-35, 12-30, 12-25, 12-20, 12-17, 12-15, 15-50, 15-40, 15-35, 15-30, 15-25, 15-20, 15-17 or 17-20 nucleotides in length. In a particular embodiment, the 3'-dimer-forming portions of the first primer and the second primer each are 5 nucleotides, 6 nucleotides, 7 nucleotides, 8 nucleotides, 9 nucleotides or 10 nucleotides in length.

In one embodiment of the present invention, each of the first primer and the second primer consists of two portions: (i) a 5'-templating portion; and (ii) a 3'-dimer-forming portion. The 5'-templating portion has a nucleotide sequence that is non-complementary to the 3'-dimer-forming portion of another dimer-forming primer.

The dimer-forming primer according to the present invention should not be blocked at the 3'-end to be extended for amplification.

The first primer and the second primer, constituting the pair of dimer-forming primers of the present invention, do not require any specific length. In one embodiment, the first primer and the second primer each are 7 to 100 nucleotides in length. In a particular embodiment, the lengths of the first primer and the second primer ranges from at least 7, 10, 15, 20, 30, 40, 60 or 80 nucleotides to no more than 100, 80, 70, 60, 50, 40, 35, 30, 25, 20, 15 or 10 nucleotides. For example, the first primer and the second primer each may be 7-40, 7-60, 7-80, 7-100, 10-40, 10-60, 10-80, 10-100, 15-40, 15-60, 15-80, 15-100, 20-40, 20-60, 20-80, 20-100, 30-40, 30-60, 30-80 or 30-100 nucleotides in length.

The first primer and the second primer, included in the dimer-forming primer pair according to the present invention, do not require any specific sequence except for the dimer-forming portion.

A dimer-forming primer of the present invention may or may not have a self-complementary sequence. Where a dimer-forming primer of the present invention has a self-complementary sequence, it may form a secondary structure, such as a hairpin-stem structure by hybridization of the self-complementary sequence. Where a dimer-forming primer of the present invention does not have a self-complementary sequence, the dimer-forming primer may form a random-coil.

In one embodiment of the present invention, the kit further comprises a label.

The first primer and the second primer are each extended by a nucleic acid polymerase to form an extended duplex; wherein a detectable signal is provided in a dependent manner on the presence of the extended duplex.

The label is (i) at least one label linked to the first primer and/or the second primer, (ii) a label incorporated into the extended duplex during the extension, (iii) a label incorporated into the extended duplex during the extension and a label linked to the first primer and/or the second primer, (iv) an intercalating label; or (v) at least one label linked to a detection oligonucleotide.

The label may be one known in the art, as long as the dimer-forming primers can provide a signal by formation of the extended duplex. The label is described in detail in the present specification.

In one embodiment, the label is an interactive dual label comprising a reporter molecule and a quencher molecule, and the interactive dual label is linked to the first primer and/or the second primer.

In another embodiment, the label is an interactive dual label comprising a reporter molecule and a quencher molecule, and one of the reporter molecule and the quencher molecule is linked to the first primer and the other is linked to the second primer.

A pair of dimer-forming primers of the present invention was found to be amplified by hybridization with each other without the use of additional templates (see Example 1). In addition, the method of the present invention was found to be useful in measuring the performance of a nucleic acid polymerase in a more sensitive manner to the units of the nucleic acid polymerase, as compared to conventional methods using a template and a primer(s) (see Example 2). Furthermore, a pair of dimer-forming primers of the present invention not only can be amplified simultaneously with the target nucleic acid sequence without affecting the amplification of the target nucleic acid sequence, but also exhibits a comparable effect to that of the conventional CesA3 internal control.

As described above, a pair of dimer-forming primers of the present invention can be used for evaluating the performance of the components including a nucleic acid polymerase, and can also be used as an internal control in the detection of the target nucleic acid sequence.

The features and advantages of this invention will be summarized as follows:

(a) Conventional methods for evaluating the activity of a nucleic acid polymerase requires reacting the nucleic acid polymerase with a template, a pair of primers for amplifying the template, and a probe for generating a signal upon the extension of the primer. In contrast, the method of the present invention allows the evaluation of the activity of a nucleic acid polymerase by an amplification reaction using a pair of dimer-forming primers instead of complex components such as templates, primers, and probes.

(b) Conventional methods require complex and sophisticated designs of templates and oligonucleotides (e.g., primer pairs and probes), taking into account the specific hybridization such as hybridization between template and primer pairs and hybridization between template and probe, and the non-specific hybridization such as hybridization between template and template, hybridization between primer and primer, hybridization between probe and probe, and hybridization between primer and probe. On the other hand, the method of the present invention uses only a pair of dimer-forming primers, which can greatly reduce considerations and is therefore simple.

(c) Unlike conventional methods, indicators (e.g., Ct value) obtained by the present invention is very sensitive to the change of the unit of a nucleic acid polymerase. Thus, the method of the present invention is useful in estimating a unit of an unknown nucleic acid polymerase.

(d) The pair of dimer-forming primers of the present invention can be used as an internal control in the detection of a target nucleic acid sequence.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Identification of Self-Amplification of Dimer-Forming Primers (DFPs)

In order to identify whether the dimer-forming primers (DFPs) of the present invention can produce amplification products by self-amplification in the absence of an additional template, the amplification reaction was carried out using the amplification composition comprising a pair of DFPs.

<1-1> Preparation of DFP Pairs #1, #2 and #3

Three DFP pairs were prepared that have dimer-forming portions of varying lengths as shown in Table 1. Specifically, the DFP pair #1 consisted of a pair of DFPs (i.e., DFP-1 and DFP-2), each having five (5) complementary nucleotides at the 3'-end part (i.e., "5'-CTGAT-3" at the 3'-end part of DFP-1 is complementary to "5'-ATCAG-3'" at the 3'-end part of DFP-2); the DFP pair #2 consisted of a pair of DFPs (i.e., DFP-1 and DFP-3), each having six (6) complementary nucleotides at the 3'-end part (i.e., "5'-GCTGAT-3" at the 3'-end part of DFP-1 is complementary to "ATCAGC" at the 3'-end part of DFP-3); and DFP pair #3 consisted of a pair of DFPs (i.e., DFP-1 and DFP-4) having seven (7) complementary nucleotides at the 3'-end part (i.e., "5'-AGCTGAT-3'" at the 3'-end part of DFP-1 is complementary to "5'-ATCAGCT-3'" at the 3'-end part of DFP-4).

To obtain a signal indicative of amplification from each DFP pair, one DFP (DFP-1) of each DFP pair was labelled with a fluorescent reporter molecule (FAM) internally and with a quencher molecule (BHQ-1) at the 5'-end.

Two DFPs of each pair form a dimer through hybridization between the 3'-dimer-forming portions under amplification conditions (particularly annealing conditions), and are each extended by the polymerization activity of the nucleic acid polymerase to form an extended duplex, thereby providing a detectable signal (see FIG. 2).

TABLE 1

| Name | Type | Sequence (5'→3') | SEQ ID NO. |
|---|---|---|---|
| DFP pair #1 | DFP-1 | 5'-[BHQ-1]TTGGCTTGGCTTGGC[T(FAM)]TTAG<u>CTGAT</u>-3' | 1 |
| | DFP-2 | 5'-GGTTCTCAAGCAACAAT<u>ATCAG</u>-3' | 2 |
| DFP pair #2 | DFP-1 | 5'-[BHQ-1]TTGGCTTGGCTTGGC[T(FAM)]TTAG<u>CTGAT</u>-3' | 1 |
| | DFP-3 | 5'-GGTTCTCAAGCAACAAT<u>ATCAGC</u>-3' | 3 |
| DFP pair #3 | DFP-1 | 5'-[BHQ-1]TTGGCTTGGCTTGGC[T(FAM)]TTA<u>AGCTGAT</u>-3' | 1 |
| | DFP-4 | 5'-GGTTCTCAAGCAACAAT<u>ATCAGCT</u>-3' | 4 |

(Underlined letters: the 5'-dimer-forming portion)

<1-2> Amplification Reaction Using DFP Pairs #1, #2 and #3

The amplification reaction was carried out by real-time PCR using the amplification composition comprising each of DFP pairs #1, #2 and #3 prepared in Example <1-1>. The DFP pairs are amplified in the absence of a template to generate a fluorescence signal, and the signal is detected in real time to obtain an amplification curve.

Specifically, the reaction was conducted in the final volume of 20 µl containing each of DFP pair #1 (5 pmole of DFP-1 and 5 pmole of DFP-2), DFP pair #2 (5 pmole of DFP-1 and 5 pmole of DFP-3) and DFP pair #3 (5 pmole of DFP-1 and 5 pmole of DFP-4) and 5 µl of 4× Master Mix containing 2.5 mM MgCl$_2$, 200 µM of dNTPs and 2 units of Taq DNA polymerase (Enzynomics, Korea); the tube containing the reaction mixture was placed in the real-time thermocycler (CFX96, Bio-Rad); the reaction mixture was denatured for 5 min at 50° C. followed by 15 min at 95° C. and subjected to 50 cycles of 10 sec at 95° C., 60 sec at 57° C., 10 sec at 72° C. Detection of the signal was performed at 57° C. of each cycle. The threshold (RFU=200) was applied to the amplification curve.

Figure 3:
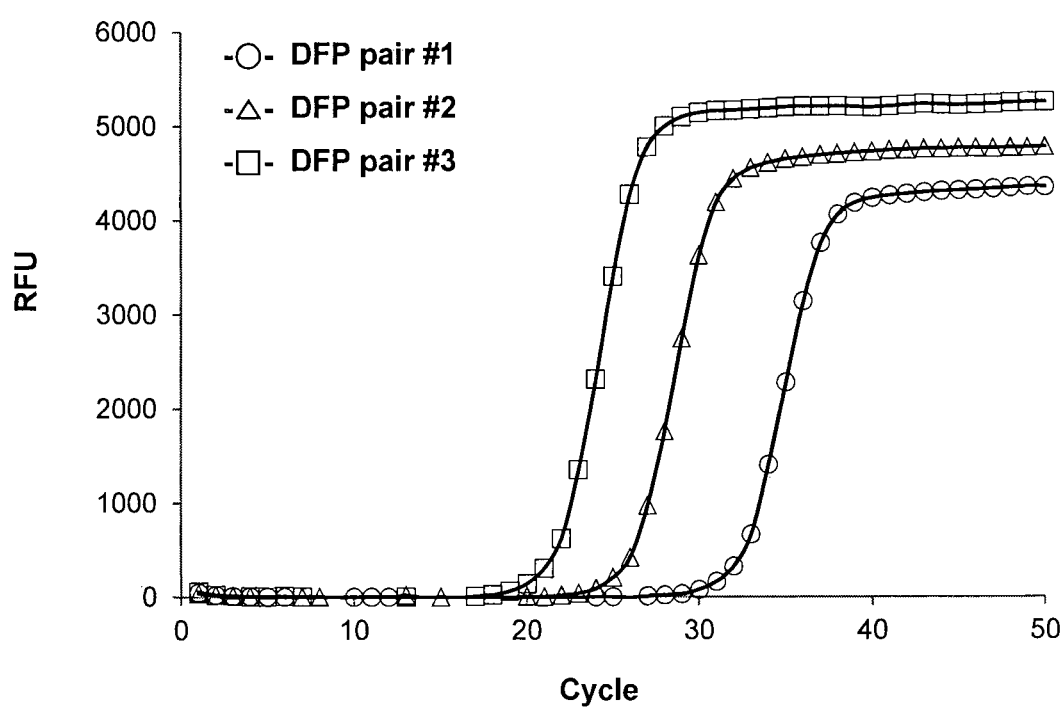
FIG. 3 shows the amplification curves obtained by amplification reactions using DFP pair #1, DFP pair #2 and DFP pair #3 with varying lengths of dimer-forming portions.

The results are shown in FIG. 3. As shown in FIG. 3, the DFP pairs #1, #2 and #3 produced typical S-shaped amplification curves as amplification cycles progressed. The results demonstrate that the DFP pairs of the invention were amplified in the absence of an additional template.

On the other hand, the DFP pairs of the invention exhibited different amplification efficiencies depending on the length of the dimer-forming portion. Specifically, the amplification curves obtained using the DFP pairs #1, #2 and #3 showed CT values of 31.23, 24.93 and 20.37, respectively. The results demonstrate that the amplification efficiency can be adjusted by the length of the dimer-forming portion in the DFP pair.

As such, the DFP pair of the present invention was found to be amplified by hybridization with each other without the use of an additional template. Thus, the DFP pair of the present invention can be used to evaluate the performance of the components (for example, a nucleic acid polymerase, a label for providing a signal, a reaction vessel, a heat block, a thermocycler, a detector, etc.) by an amplification reaction.

Example 2

Performance Evaluation of Nucleic Acid Polymerase Using DFP Pair

In this Example, we examined whether the DFP pair according to the present invention can be used to evaluate the performance of a nucleic acid polymerase, the polymerization activity.

<2-1> Preparation of DFP Pair #4

To evaluate the performance of a nucleic acid polymerase, DFP pair #4 according to the present invention was prepared (see Table 2).

The DFP pair #4 consisted of two DFPs, i.e., DFP-5 (SEQ ID NO: 5) and DFP-6 (SEQ ID NO: 6), each having five (5) complementary nucleotides at the 3'-end part.

To obtain a signal indicative of amplification from the DFP pair, DFP-5 was labelled with a fluorescent reporter molecule (CAL Fluor Red 610) internally and with a quencher molecule (BHQ-2) at the 5'-end.

Meanwhile, a template (a genomic DNA of *Neisseria gonorrhoeae* (NG)), a primer pair, i.e., a forward primer (NG-F; SEQ ID NO: 7) and a reverse primer (NG-R; SEQ ID NO: 8), which are capable of amplifying the template, and a probe (NG-P; SEQ ID NO: 9) for detecting the amplification were prepared as a control. The probe was labelled with a fluorescent reporter molecule (CAL Fluor Red 610) at the 5'-end and with a quencher molecule (BHQ-2) at the 3'-end. The mixture was designated as "Control #1".

TABLE 2

| Name | Type | Sequence (5'→3') | SEQ ID NO. |
|---|---|---|---|
| DFP pair #4 | DFP-5 | 5'-[Cal Fluor Red 610]TTACCATACCATACC[T(BHQ-2)]TTTTGCGAG-3' | 5 |
| | DFP-6 | 5'-CAATGGATCGGTATCACTCGC-3' | 6 |
| Control #1 | NG-F | 5'-TACGCCTGCTACTTTCACGCTIIIIIGTAATCAGATG-3' | 7 |
| | NG-R | 5'-CAATGGATCGGTATCACTCGCIIIIICGAGCAAGAAC-3' | 8 |
| | NG-P | 5'-[Cal Fluor Red 610]TGCCCCTCATTGGCGTGTTTCG[BHQ-2]-3' | 9 |
| | Template | Genomic DNA of *Neisseria gonorrhoeae* (NG) | — |

(Underlined letters: the 5'-dimer-forming portion)
(I: deoxyinosine)

<2-2> Evaluation of Polymerization Activity of Nucleic Acid Polymerase Using DFP Pair The amplification reaction was performed by real-time PCR using the amplification composition comprising the DFP pair #4 prepared in Example <2-1>. For comparison, an additional amplification reaction was performed under the same conditions using the amplification composition comprising the control #1 prepared in Example <2-1>.

In particular, in order to examine whether the DFP pair #4 and the control group #1 can yield different indicators by changes in units of the nucleic acid polymerase, various units of nucleic acid polymerase were used in the amplification reaction.

Specifically, the reaction was conducted in the final volume of 20 µl containing each of DFP pair #4 (5 pmole of DFP-4 and 5 pmole of DFP-5) and Control #1 (10 pg of NG genomic DNA, 5 pmole of NG-F, 5 pmole of NG-R, and 3 pmole of NG-P), 2 µl of 10× Hot-start PCR buffer (Thermo Scientific, USA), 2 µl of 10× MgCl$_2$ (2 mM MgCl$_2$), 200 µM of dNTPs and 4 µl of Maxima Hot Start Taq DNA polymerase (4 U, 2 U, 1 U, 0.5 U, and 0.1 U) (Thermo Scientific, USA); the tube containing the reaction mixture was placed in the real-time thermocycler (CFX96, Bio-Rad); the reaction mixture was denatured for 4 min at 95° C. and subjected to 45 cycles of 10 sec at 95° C., 60 sec at 57° C., 10 sec at 72° C. Detection of the signal was performed at 57° C. of each cycle. The threshold (RFU=500) was applied to the amplification curve. Ct (cycle threshold) value was used as an indicator indicative of amplification.

Figure 4:
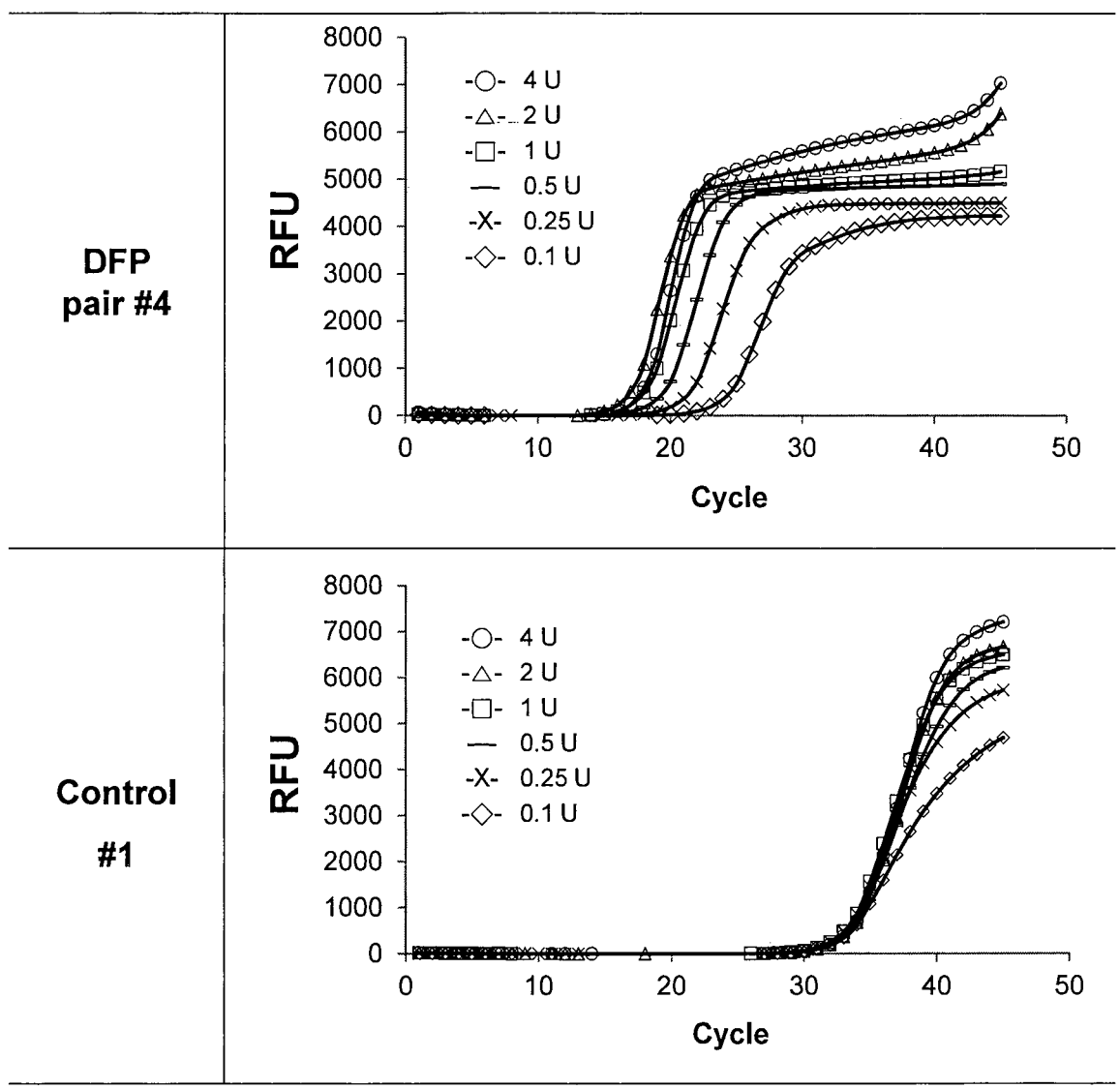
FIG. 4 shows the amplification curves obtained by amplification reactions using various units of nucleic acid polymerase and DFP pair #4 (consisting of DFP-5 and DFP-6) (top panel); and using various units of nucleic acid polymerase and DFP pair #1 (consisting of a NG template, NG-F, NG-R and NG-P) (bottom panel).

The results are shown in FIG. 4. In the figure, the top panel represents the amplification curves obtained by the amplification reactions using the DFP pair #4; and the bottom panel represents the amplification curves obtained by the amplification reactions using the Control #1.

As shown in FIG. 4, both the DFP pair #4 and the control #1 produced sigmoid amplification curves by PCR. However, with regard to the unit change of the nucleic acid polymerase, the Control #1 showed a constant Ct value (constant amplification efficiency) despite the increase in the unit of the nucleic acid polymerase; whereas the DFP pair #4 showed a decrease in the Ct value (increased amplification efficiency) with increasing units of nucleic acid polymerase.

The change in the amplification efficiency according to the unit of the nucleic acid polymerase was calculated as follows.

Change in the amplification efficiency according to the unit of the nucleic acid polymerase (ΔCt)= (Ct value for 0.1 unit of nucleic acid polymerase)−(Ct value for 4 unit of nucleic acid polymerase)

The results are shown in Table 3.

TABLE 3

| | | Ct | | | | | | |
|---|---|---|---|---|---|---|---|---|
| Unit of polymerase | | 4 U | 2 U | 1 U | 0.5 U | 0.25 U | 0.1 U | ΔCt |
| Composition | DFP pair #4 | 17.74 | 16.97 | 18.02 | 19.39 | 21.39 | 24.46 | 6.72 |
| | Control #1 | 33.35 | 33.42 | 33.05 | 33.35 | 33.06 | 33.58 | 0.23 |

As shown in Table 3, for the DFP pair #4, the change in the amplification efficiency (ΔCt) was 6.72, indicating that the amplification efficiency was sensitive to changes in the unit of the nucleic acid polymerase. In contrast, for the control #1, the change in the amplification efficiency (ΔCt) was 0.23, indicating that the amplification efficiency did not change despite changes in the unit of the nucleic acid polymerase.

The above results show that the conventional methods using a template and primers as in the control #1 has a limitation in accurately evaluating the polymerization activity of the nucleic acid polymerase. In contrast, the method using the DFP pair according to the present invention was found to be more useful in measuring the polymerization activity of the nucleic acid polymerase, since the amplification efficiency is sensitive to the change of the unit of the nucleic acid polymerase.

According to the present invention, the performance of a nucleic acid polymerase can be evaluated by reacting the DFP pair with a certain amount of the nucleic acid polymerase to obtain an indicator indicative of amplification, such as Ct value. In addition, the performance of the polymerization activity of the nucleic acid polymerase can be evaluated by comparing the indicator obtained from the reaction using the nucleic acid polymerase with a reference indicator obtained from a reference reaction using a reference nucleic acid polymerase.

Example 3

Use of DFP Pair as an Internal Control

It was examined whether the DFP pair according to the present invention could be used as an internal control in the detection of a target nucleic acid sequence.

For this purpose, simultaneous amplification of the DFP pair and the NG target nucleic acid sequence (using target-specific primers and a target-specific probe) was performed to confirm whether the amplification of the DFP pair is independent on the amplification of the NG target nucleic acid sequence.

In order for the DFP pair to be used as an internal control for the amplification reaction of the target nucleic acid sequence, the amplification efficiency of the NG target nucleic acid sequence should not be affected by the presence of the DFP pair, and vice versa.

<3-1> Preparation of Control #1, Control #1+CesA3 and Control #1+DFP Pair #1

For this experiment, three compositions were prepared: (i) a composition for amplifying only a target nucleic acid sequence; (ii) a composition for simultaneously amplifying a target nucleic acid sequence and CesA3 as a conventional internal control; and (iii) a composition for simultaneously amplifying a target nucleic acid sequence and a DFP pair of the present invention as an internal control.

Specifically, the composition for amplifying only a target nucleic acid sequence consisted of NG target nucleic acid sequence, primers for amplifying the target (NG-F, SEQ ID NO: 7; NG-R, SEQ ID NO: 8) and a probe for detecting the amplified targets (NG-P, SEQ ID NO: 9), which was designated as "Control #1".

In addition, the composition for simultaneously amplifying a target nucleic acid sequence and CesA3 consisted of the Control #1, and a plasmid DNA containing CesA3 (cellulose synthase 3) gene from *Arabidopsis*, primers for amplifying CesA3 (CesA3-F, SEQ ID NO: 10; CesA3-R, SEQ ID NO: 11) and a probe for detecting the amplified CesA3 (CesA3-P, SEQ ID NO: 12), which was designated as "Control #1+CesA3". The probe (CesA3-P) was labelled with a fluorescent reporter molecule (Quasar 670) at the 5'-end and with a quencher molecule (BHQ-3) at the 3'-end.

Further, the composition for simultaneously amplifying a target nucleic acid sequence and a DFP pair consisted of the Control #1, and the DFP pair (DFP-1, SEQ ID NO: 1; DFP-2, SEQ ID NO: 2) prepared in Example <1-1>, which was designated as "Control #1+DFP pair #1".

The types and sequences of oligonucleotides in the compositions as prepared above are listed in Table 4.

TABLE 4

| Name | Type | Sequence (5'→3') | SEQ ID NO. |
|---|---|---|---|
| Control #1 | NG-F | 5'-TACGCCTGCTACTITCACGCTIIIIIGTAATCAGATG-3' | 7 |
| | NG-R | 5'-CAATGGATCGGTATCACTCGCIIIIICGAGCAAGAAC-3' | 8 |

TABLE 4-continued

| Name | Type | Sequence (5'→3') | SEQ ID NO. |
|---|---|---|---|
| | NG-P | 5'-[Cal Fluor Red 610]TGCCCCTCATTGGCGTGTTTCG[BHQ-2]-3' | 9 |
| | Target | a genomic DNA of Neisseria gonorrhoeae (NG) | — |
| Control #1 + CesA3 | NG-F | 5'-TACGCCTGCTACTTTCACGCTIIIIIGTAATCAGATG-3' | 7 |
| | NG-R | 5'-CAATGGATCGGTATCACTCGCIIIIICGAGCAAGAAC-3' | 8 |
| | NG-P | 5'-[Cal Fluor Red 610]TGCCCCTCATTGGCGTGTTTCG[BHQ-2]-3' | 9 |
| | Target | a genomic DNA of Neisseria gonorrhoeae (NG) | — |
| | CesA3-F | 5'-ATGGAATCCGAAGGAGAAACCIIIIIAAAGCCGATG-3' | 10 |
| | CesA3-R | 5'-TCCTCTCATACTCGTAGCAAGGCIIIIIAACTGGGAATG-3' | 11 |
| | CesA3-P | 5'-[Quasar 670]TCTGGCAAGTCTGCGGAACAATG[BHQ-3]-3' | 12 |
| | Internal control | a plasmid containing CesA3 gene | — |
| Control #1 + DFP pair #1 | NG-F | 5'-TACGCCTGCTACTTTCACGCTIIIIIGTAATCAGATG-3' | 7 |
| | NG-R | 5'-CAATGGATCGGTATCACTCGCIIIIICGAGCAAGAAC-3' | 8 |
| | NG-P | 5'-[Cal Fluor Red 610]TGCCCCTCATTGGCGTGTTTCG[BHQ-2]-3' | 9 |
| | Target | a genomic DNA of Neisseria gonorrhoeae (NG) | — |
| | DFP-1 | 5'-[BHQ-1]TTGGCTTGGCTTGGC[T(FAM)]TTAGCTGAT-3' | 1 |
| | DFP-2 | 5'-GGTTCTCAAGCAACAATATCAG-3' | 2 |

(I: deoxyinosine)

<3-2> Simultaneous Amplification of DFP Pair and NG Target Nucleic Acid Sequence The amplification reaction was performed by real-time PCR using each composition prepared in Example <3-1>. A Taq DNA polymerase having a 5' nuclease activity was used for simultaneous amplification of the DFP pair and the target nucleic acid sequence and the cleavage of the probe.

Specifically, the reaction was conducted in the final volume of 20 μl containing each of the Control #1 (5 pmole of NG-F, 5 pmole of NG-R, 3 pmole of NG-P, and 100, 10 or 1 or 0 pg of NG genomic DNA), the Control #1+CesA3 (5 pmole of NG-F, 5 pmole of NG-R, 3 pmole of NG-P, 100, 10, 1 or 0 pg of NG genomic DNA, 5 pmole of CesA3-F, 5 pmole of CesA3-R, 3 pmole of CesA3-P, and 0.1 pg of CesA3 plasmid DNA), and the Control #1+DFP pair #1 (5 pmole of NG-F, 3 pmole of NG-P, 100, 10, 1, or 0 pg of NG genomic DNA, 5 pmole of DFP-1, and 5 pmole of DFP-2) and 5 μl of 4× Master Mix containing 2 mM MgCl₂, 200 μM of dNTPs and 2 units of Taq DNA polymerase (Enzynomics, Korea); the tube containing the reaction mixture was placed in the real-time thermocycler (CFX96, Bio-Rad); the reaction mixture was denatured for 5 min at 50° C. followed by 15 min at 95° C. and subjected to 50 cycles of 10 sec at 95° C., 60 sec at 57° C., 10 sec at 72° C. Detection of the signal was performed at 57° C. of each cycle. The thresholds of RFU 400, RFU 500 and RFU 100 were applied to the amplification curves obtained using a FAM label, a CAL Fluor 610 label, and a Quasar 670 label, respectively.

Figure 5:
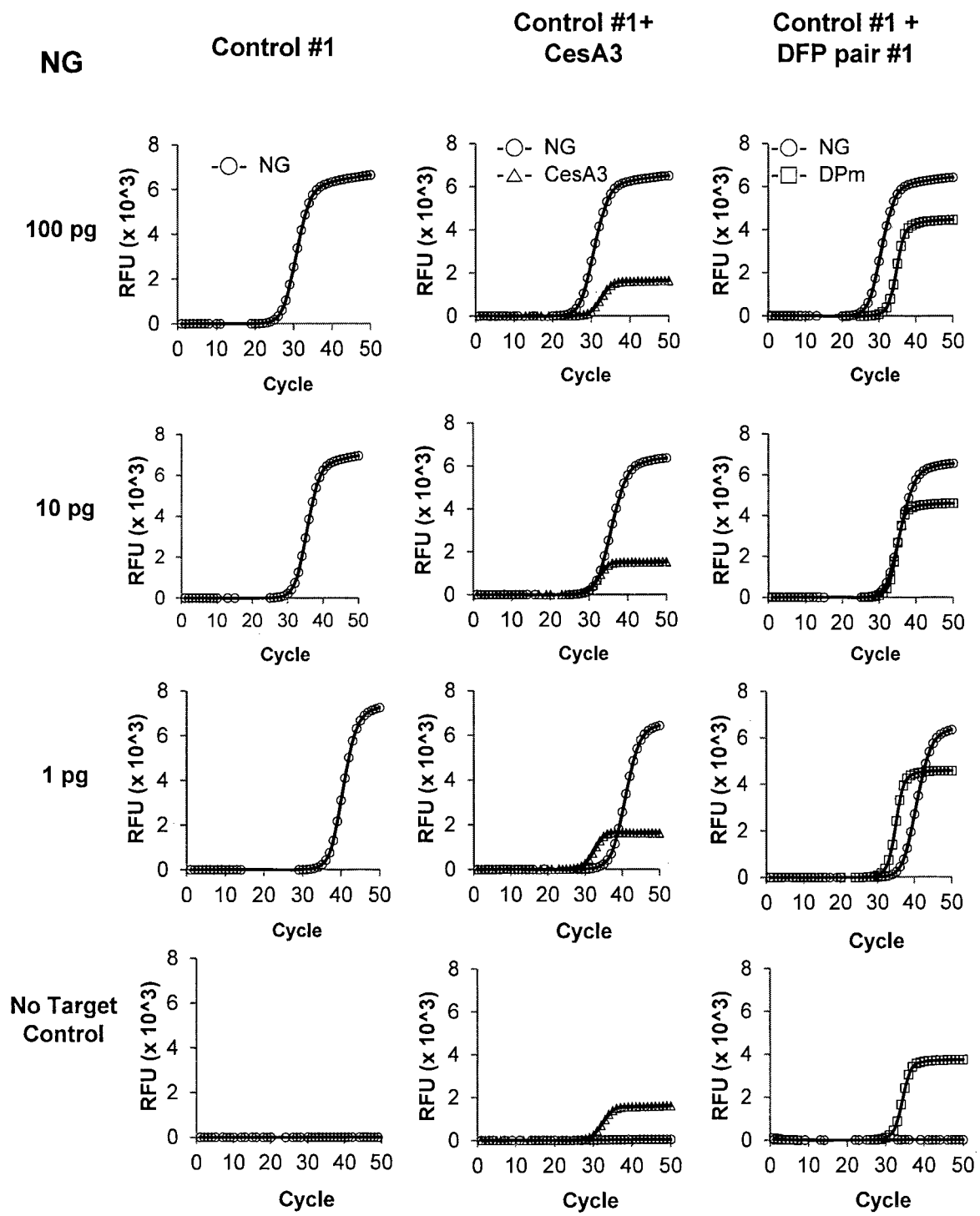
FIG. 5 shows the amplification curves for target nucleic acid sequence (denoted by "—O—") and for internal control (denoted by "-Δ-" or "-□-"), obtained by amplification reactions using various concentrations (100 pg, 10 pg, 1 pg, or NTC) of target nucleic acid sequence (NG) in the presence or absence of an internal control. In the figure, "Control #1" represents the amplification results obtained by using various concentrations of target nucleic acid sequence (NG) in the absence of an internal control (left column); "Control #1+CesA3" represents the amplification results obtained by using various concentrations of target nucleic acid sequence (NG) in the presence of CesA3 as an internal control (middle column); and "Control #1+DFP pair #1" represents the amplification results obtained by using various concentrations of target nucleic acid sequence (NG) in the presence of DFP pair #1 as an internal control (right column).

The results are shown in FIG. 5 and Table 5.

As shown in FIG. 5 and Table 5, the amplification curves for target nucleic acid sequence (denoted by "—O—" in the figure) obtained using each of the Control #1, the Control #1+CesA3, and the Control #1+DFP pair #1 showed decreased Ct values with increased concentrations of NG target genome and a similar Ct value at the same concentration of NG target genome.

On the other hand, the amplification curves for each internal control (denoted by "-Δ-" or "-□-" in the figure) shows a similar Ct value, regardless of the concentration of NG target genome.

Specifically, the Ct value of the target nucleic acid sequence showed a difference of 0.01, 0.14, or 0.06 (ΔCt) between the Control #1 and the Control #1+CesA3 for 100 pg, 10 pg or 1 pg of the target nucleic acid sequence. Further, the Ct value of the target nucleic acid sequence showed a difference of −0.01, 0.03 and −0.05 (ΔCt) between the Control #1 and the Control #1+DFP pair #1 for 100 pg, 10 pg or 1 pg of the target nucleic acid sequence. The results demonstrate that amplification of the target nucleic acid sequence was not affected by the presence or amplification of an internal control, CesA3 or DFP pair.

On the other hand, the Ct value of the internal control (CesA3) showed a maximum difference of 0.27 (ΔCt) between 100 pg, 10 pg and 1 pg of the target nucleic acid sequence; the Ct value of the internal control (DFP pair) showed a maximum difference of 0.24 (ΔCt) between 100 pg, 10 pg and 1 pg of the target nucleic acid sequence. The results demonstrate that amplification of the internal control

TABLE 5

| | | Composition | | | | |
|---|---|---|---|---|---|---|
| | | Control #1 | Control #1 + CesA3 | | Control #1 + DFP pair #1 | |
| Detection | | Target Ct | Target Ct | Internal control (CesA3) Ct | Target Ct | Internal control (DFP pair) Ct |
| Concentration of template | 100 pg | 26.60 | 26.61 | 28.67 | 26.59 | 32.01 |
| | 10 pg | 31.28 | 31.42 | 28.51 | 31.31 | 31.85 |
| | 1 pg | 36.22 | 36.28 | 28.42 | 36.17 | 32.08 |
| | NTC | — | — | 28.40 | — | 31.84 |

(NTC: no target control)

was not affected by the presence, concentration or amplification of an internal control, CesA3 or DFP pair.

As described above, the DFP pair according to the present invention was found to be amplified simultaneously with the target nucleic acid sequence without affecting or being affected by the amplification of the target nucleic acid sequence. In addition, the DFP pair according to the present invention was found to have a comparable effect to the CesA3, a conventional internal control. This demonstrates that the DFP pair according to the present invention can be used as an internal control equivalent to the CesA3. Further, the DFP pair of the present invention is expected to be more effective in reducing non-specific dimer formation under the condition of amplifying multiple target nucleic acid sequences such as a multiplex PCR, compared with conventional internal controls.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for evaluating the polymerization activity of a nucleic acid polymerase in an amplification composition or an amplification device by an amplification reaction using a pair of dimer-forming primers, comprising the steps of:
   (a) providing an amplification composition comprising a pair of dimer-forming primers; wherein the pair of dimer-forming primers comprises a first primer and a second primer; wherein the first primer and the second primer each comprise a 3'-dimer-forming portion, and a nucleotide sequence of the 3'-dimer-forming portion in the first primer is complementary to a nucleotide sequence of the 3'-dimer-forming portion in the second primer, wherein the 3'-dimer forming portions of the first primer and the second primer each are 3 to 20 nucleotides in length;
   (b) subjecting the amplification composition to an amplification reaction in an amplification device; wherein the first primer and the second primer form a dimer through hybridization between the 3'-dimer-forming portions under amplification conditions, and are each extended by the nucleic acid polymerase to form an extended duplex; wherein a detectable signal is provided in a dependent manner on the presence of the extended duplex;
   (c) detecting the detectable signal during or after the amplification reaction;
   (d) obtaining an indicator indicative of amplification from the detected signal; and
   (e) evaluating the polymerization activity of the nucleic acid polymerase based on the indicator obtained;
   wherein the method is performed in the absence of an additional template hybridizable with the first primer and the second primer.

2. The method of claim 1, wherein the polymerization activity of the nucleic acid polymerase is determined by comparing the indicator obtained with a reference indicator obtained from a reference reaction.

3. The method of claim 1, wherein the indicator is selected from the group consisting of Ct (cycle threshold), ΔRFU, RFU ratio, End-RFU, a melting peak height, a melting peak width, a melting peak area, and a combination thereof.

4. The method of claim 1, wherein the first primer and the second primer each are 7 to 100 nucleotides in length.

5. The method of claim 1, wherein the 3'-dimer forming portions of the first primer and the second primer each comprise one or more non-complementary nucleotides.

6. The method of claim 1, wherein the detectable signal is provided by (i) at least one label linked to the first primer and/or the second primer, (ii) a label incorporated into the extended duplex during the extension, (iii) a label incorporated into the extended duplex during the extension and a label linked to the first primer and/or the second primer, (iv) an intercalating label; or (v) at least one label linked to a detection oligonucleotide.

7. The method of claim 6, wherein the signal is provided by at least one label linked to a detection oligonucleotide upon the formation of a duplex comprising the detection oligonucleotide or the cleavage of the detection oligonucleotide.

8. The method of claim 1, wherein the amplification reaction further comprises denaturing the extended duplex, hybridizing denatured strands with the first primer and the second primer, and extending the first primer and the second primer to form the extended duplex.

9. The method of claim 1, the detection of the signal is performed at one or more detection temperatures.

10. The method of claim 1, wherein the method further comprises melting the extended duplex or melting the extended duplex followed by hybridization between the steps (b) and (c) to provide a detectable signal, and the step (c) is performed by detecting the signal provided by the melting or the melting followed by hybridization.

* * * * *

```
                            SEQUENCE LISTING

<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide: DFP-1

<400> SEQUENCE: 1
ttggcttggc ttggctttag ctgat                                            25

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide: DFP-2

<400> SEQUENCE: 2
ggttctcaag caacaatatc ag                                               22

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide: DFP-3

<400> SEQUENCE: 3
ggttctcaag caacaatatc agc                                              23

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide: DFP-4

<400> SEQUENCE: 4
ggttctcaag caacaatatc agct                                             24

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide: DFP-5

<400> SEQUENCE: 5
ttaccatacc atacctttt gcgag                                             25
```

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide: DFP-6

<400> SEQUENCE: 6
caatggatcg gtatcactcg c                                         21

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide: NG-F

<400> SEQUENCE: 7
tacgcctgct actttcacgc tgtaatcaga tg                             32

<210> SEQ ID NO 8
<211> LENGTH: 32
<212> TYPE: DNA
<213> ORGANISM: Artificial Sequence
<220> FEATURE:
<223> OTHER INFORMATION: Synthetic oligonucleotide: NG-R

<400> SEQUENCE: 8
caatggatcg gtatcactcg ccgagcaaga ac                             32

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide: NG-P

<400> SEQUENCE: 9
tgcccctcat tggcgtgttt cg                                        22

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide: CesA3-F
<220> FEATURE:
<221> NAME/KEY: misc_feature
<222> LOCATION: (22)..(26)
<223> OTHER INFORMATION: n is deoxyinosine

<400> SEQUENCE: 10
atggaatccg aaggagaaac cnnnnnaaag ccgatg                         36

<210> SEQ ID NO 11
<211> LENGTH: 39
<212> TYPE: DNA
<213> ORGANISM: Artificial Sequence
<220> FEATURE:
<223> OTHER INFORMATION: Synthetic oligonucleotide: CesA3-R
<220> FEATURE:
<221> NAME/KEY: misc_feature
<222> LOCATION: (24)..(28)
<223> OTHER INFORMATION: n is deoxyinosine

<400> SEQUENCE: 11

```
tcctctcata ctcgtagcaa ggcnnnnnaa ctgggaatg                    39
```

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide: CesA3-P

<400> SEQUENCE: 12

```
tctggcaagt ctgcggaaca atg                                     23
```